United States Patent
Nardo et al.

(10) Patent No.: US 12,115,097 B2
(45) Date of Patent: Oct. 15, 2024

(54) PATIENT WARMING SYSTEM

(71) Applicant: American Sterilizer Company, Mentor, OH (US)

(72) Inventors: Richard P. Nardo, Highland Heights, OH (US); Farhad Haghgoeian, Solon, OH (US); Andrew Moss, Solon, OH (US); John Michael Kasunich, Mayfield Heights, OH (US); Damon Jurkiewicz, Cleveland, OH (US); James T. Dacek, Westlake, OH (US); Gabor Louis Toth, Columbus, OH (US)

(73) Assignee: American Sterilizer Company, Mentor, OH (US)

( * ) Notice: Subject to any disclaimer, the term of this patent is extended or adjusted under 35 U.S.C. 154(b) by 758 days.

(21) Appl. No.: 17/162,379

(22) Filed: Jan. 29, 2021

(65) Prior Publication Data

US 2021/0236326 A1 Aug. 5, 2021

Related U.S. Application Data

(60) Provisional application No. 62/968,628, filed on Jan. 31, 2020.

(51) Int. Cl.
*A61F 7/00* (2006.01)
*G16H 20/30* (2018.01)
(Continued)

(52) U.S. Cl.
CPC .............. *A61F 7/00* (2013.01); *G16H 20/30* (2018.01); *G16H 40/63* (2018.01);
(Continued)

(58) Field of Classification Search
None
See application file for complete search history.

(56) References Cited

U.S. PATENT DOCUMENTS 2,473,183 A 6/1949 Watson
3,900,654 A 8/1975 Stinger
(Continued)

FOREIGN PATENT DOCUMENTS

CA 2136066 A1 11/1993
CN 107802400 A 3/2018
(Continued)

OTHER PUBLICATIONS

International Preliminary Report on Patentability for related International Application No. PCT/US2021/015725 mailed Aug. 11, 2022.
(Continued)

*Primary Examiner* — Tigist S Demie
(74) *Attorney, Agent, or Firm* — Renner, Otto, Boisselle & Sklar, LLP

(57) ABSTRACT

A patient warming system includes a control unit coupled to one or more warming devices. The control unit may control application of power to the heating elements of the warming devices. The control unit may provide hardware and/or software approaches to monitor and detect an overtemperature situation and/or fault of a given warming device.

17 Claims, 19 Drawing Sheets

(51) Int. Cl.
*G16H 40/63* (2018.01)
*A61F 7/08* (2006.01)

(52) U.S. Cl.
CPC .......... *A61F 2007/0086* (2013.01); *A61F 2007/0093* (2013.01); *A61F 2007/0096* (2013.01); *A61F 7/08* (2013.01)

(56) References Cited

U.S. PATENT DOCUMENTS

| | | | |
|---|---|---|---|
| 4,061,898 | A | 12/1977 | Murray et al. |
| 4,479,795 | A | 10/1984 | Mustacich et al. |
| 4,534,886 | A | 8/1985 | Kraus et al. |
| 5,008,515 | A | 4/1991 | McCormack |
| 5,125,238 | A | 6/1992 | Ragan et al. |
| 5,422,462 | A | 6/1995 | Kishimoto |
| 5,643,480 | A | 7/1997 | Gustavsson et al. |
| 6,073,284 | A | 6/2000 | Borders |
| 6,078,026 | A | 6/2000 | West |
| 6,093,910 | A | 7/2000 | McClintock et al. |
| 6,149,674 | A | 11/2000 | Borders |
| 6,172,344 | B1 | 1/2001 | Gordon et al. |
| 6,194,692 | B1 | 2/2001 | Oberle |
| 6,235,049 | B1 | 5/2001 | Nazerian |
| 6,331,695 | B1 | 12/2001 | West |
| 6,346,189 | B1 | 2/2002 | Dai et al. |
| 6,483,087 | B2 | 11/2002 | Gardner et al. |
| 6,541,744 | B2 | 4/2003 | Von Arx et al. |
| 6,581,400 | B2 | 6/2003 | Augustine et al. |
| 6,582,456 | B1 | 6/2003 | Hand et al. |
| 6,653,607 | B2 | 11/2003 | Ellis et al. |
| 6,664,512 | B2 | 12/2003 | Horey et al. |
| 6,703,845 | B2 | 3/2004 | Stanley et al. |
| 6,706,402 | B2 | 3/2004 | Rueckes et al. |
| 6,781,166 | B2 | 8/2004 | Lieber et al. |
| 6,803,543 | B2 | 10/2004 | Argersinger et al. |
| 6,814,889 | B1 | 11/2004 | O'Grady et al. |
| 6,919,592 | B2 | 7/2005 | Segal et al. |
| 6,924,467 | B2 | 8/2005 | Ellis et al. |
| 6,933,409 | B1 | 8/2005 | Poojary et al. |
| 6,933,469 | B2 | 8/2005 | Ellis et al. |
| 6,967,309 | B2 | 11/2005 | Wyatt et al. |
| 6,974,935 | B2 | 12/2005 | O'Grady |
| 7,001,416 | B2 | 2/2006 | Augustine et al. |
| 7,022,950 | B2 | 4/2006 | Haas et al. |
| 7,053,344 | B1 | 5/2006 | Surjan et al. |
| 7,060,241 | B2 | 6/2006 | Glatkowski |
| 7,176,419 | B2 | 2/2007 | Ellis et al. |
| 7,191,482 | B2 | 3/2007 | Romano et al. |
| 7,196,289 | B2 | 3/2007 | Ellis et al. |
| 7,202,443 | B2 | 4/2007 | Rock et al. |
| 7,211,772 | B2 | 5/2007 | Carpino, II et al. |
| 7,372,006 | B2 | 5/2008 | Aisenbrey |
| 7,416,699 | B2 | 8/2008 | Dai et al. |
| 7,468,332 | B2 | 12/2008 | Avloni |
| 7,543,344 | B2 | 6/2009 | Augustine et al. |
| 7,663,076 | B2 | 2/2010 | Tarry |
| 7,714,255 | B2 | 5/2010 | Augustine et al. |
| 7,745,810 | B2 | 6/2010 | Rueckes et al. |
| 7,786,408 | B2 | 8/2010 | Augustine et al. |
| 7,851,729 | B2 | 12/2010 | Augustine et al. |
| 8,016,779 | B2 | 9/2011 | Brown et al. |
| 8,062,343 | B2 | 11/2011 | Augustine et al. |
| 8,153,940 | B2 | 4/2012 | Niemz et al. |
| 8,283,602 | B2 | 10/2012 | Augustine et al. |
| 8,581,158 | B2 | 11/2013 | Heintz et al. |
| 8,624,164 | B2 | 1/2014 | Deibel et al. |
| 8,772,676 | B2 | 7/2014 | Augustine et al. |
| 9,191,997 | B2 | 11/2015 | Weib |
| 9,468,045 | B2 | 10/2016 | Zhang et al. |
| 9,642,404 | B2 | 5/2017 | Giles et al. |
| 9,687,093 | B2 | 6/2017 | Giles et al. |
| 9,693,891 | B2 | 7/2017 | MacIntyre-Ellis et al. |
| 2004/0010246 | A1* | 1/2004 | Takahashi .............. A61M 1/77 606/1 |
| 2004/0173028 | A1 | 9/2004 | Rix |
| 2005/0187527 | A1 | 8/2005 | Rix |
| 2006/0052852 | A1 | 3/2006 | Wyatt et al. |
| 2006/0060198 | A1* | 3/2006 | Aylsworth .......... A61B 5/0205 128/204.23 |
| 2006/0062815 | A1 | 3/2006 | Djie |
| 2008/0249447 | A1 | 10/2008 | Brown et al. |
| 2008/0255538 | A1 | 10/2008 | Ellis |
| 2008/0255641 | A1 | 10/2008 | Ellis |
| 2009/0062873 | A1* | 3/2009 | Wu .................... A61B 18/1206 607/2 |
| 2012/0279953 | A1 | 11/2012 | Augustine et al. |
| 2013/0060308 | A1 | 3/2013 | Ellis |
| 2013/0073012 | A1 | 3/2013 | Ellis |
| 2013/0186884 | A1 | 7/2013 | Barfuss et al. |
| 2013/0237983 | A1 | 9/2013 | Giles et al. |
| 2014/0055239 | A1* | 2/2014 | Mohn ...................... A61F 7/02 340/6.1 |
| 2014/0261447 | A1 | 9/2014 | Giles |
| 2014/0277306 | A1 | 9/2014 | Giles |
| 2015/0290027 | A1 | 10/2015 | Augustine et al. |
| 2015/0327332 | A1 | 11/2015 | Augustine et al. |
| 2015/0366367 | A1 | 12/2015 | Augustine et al. |
| 2015/0373781 | A1 | 12/2015 | Augustine et al. |
| 2016/0081846 | A1 | 3/2016 | Katzenstein |
| 2016/0143091 | A1 | 5/2016 | Augustine et al. |
| 2017/0028196 | A1 | 2/2017 | Stopperan |
| 2017/0231811 | A1* | 8/2017 | Cubon ................. A61F 7/0097 607/110 |
| 2017/0298567 | A1 | 10/2017 | Abula |
| 2018/0193185 | A1* | 7/2018 | Thomas .................. A61F 7/02 |
| 2019/0365562 | A1 | 12/2019 | Russell |

FOREIGN PATENT DOCUMENTS

| | | |
|---|---|---|
| WO | 03011128 A1 | 2/2003 |
| WO | 2003088881 A2 | 10/2003 |
| WO | 2008033147 A1 | 3/2008 |
| WO | 2010086740 A1 | 8/2010 |
| WO | 2011084957 A1 | 7/2011 |
| WO | 2011157394 A1 | 12/2011 |
| WO | 2013134477 A1 | 9/2013 |
| WO | 2014152227 A1 | 9/2014 |
| WO | 2016113633 A1 | 7/2016 |
| WO | 2017058620 A1 | 4/2017 |
| WO | 2017068416 A1 | 4/2017 |
| WO | 2017216631 A2 | 12/2017 |

OTHER PUBLICATIONS

PCT/US2021/015725; PCT International Search Report and Written Opinion of the International Searching Authority mailed Sep. 1, 2021.

* cited by examiner

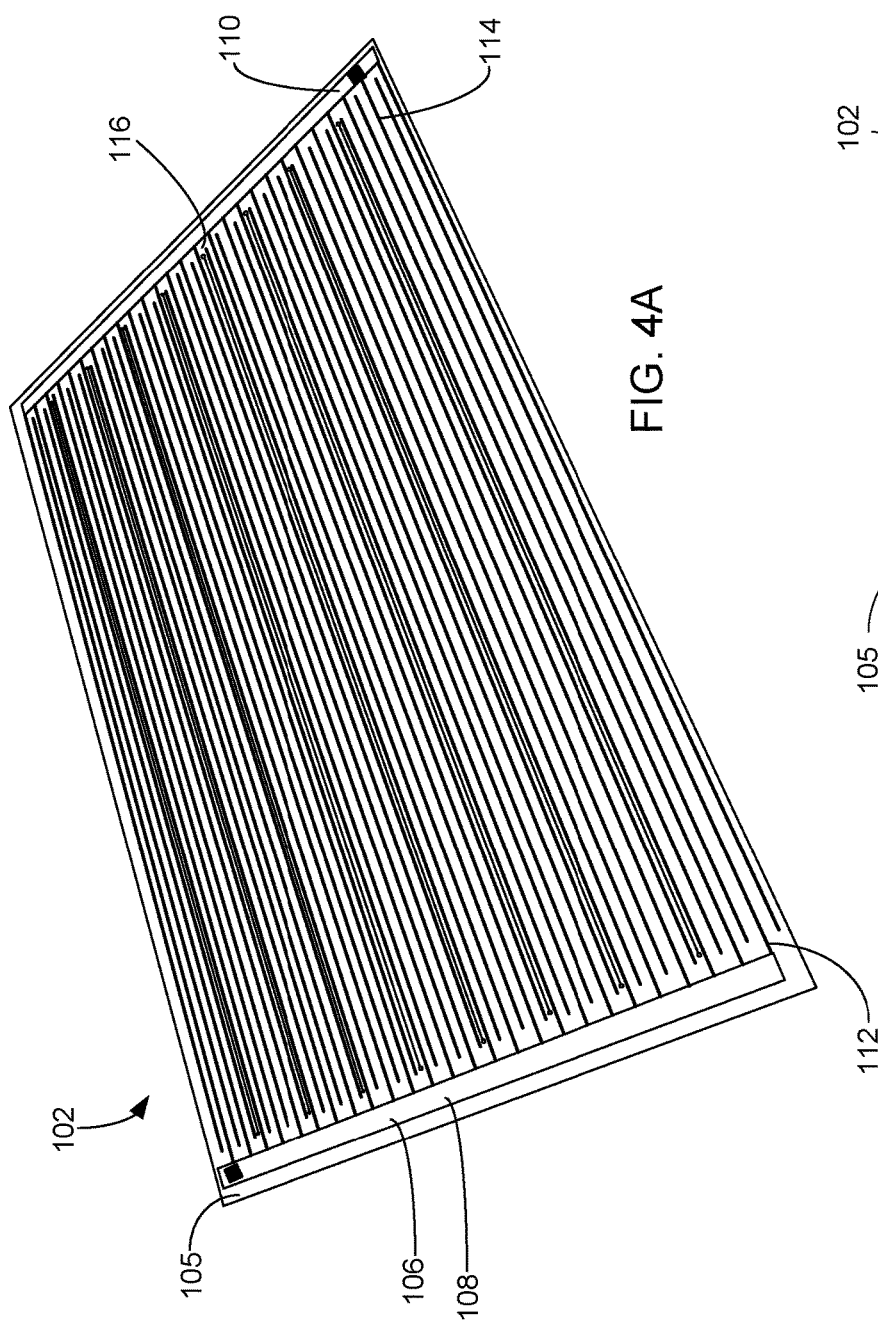
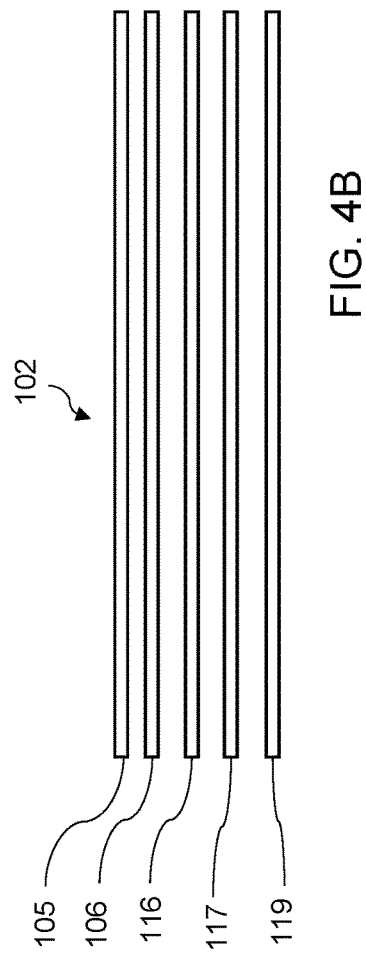
FIG. 4A
FIG. 4B

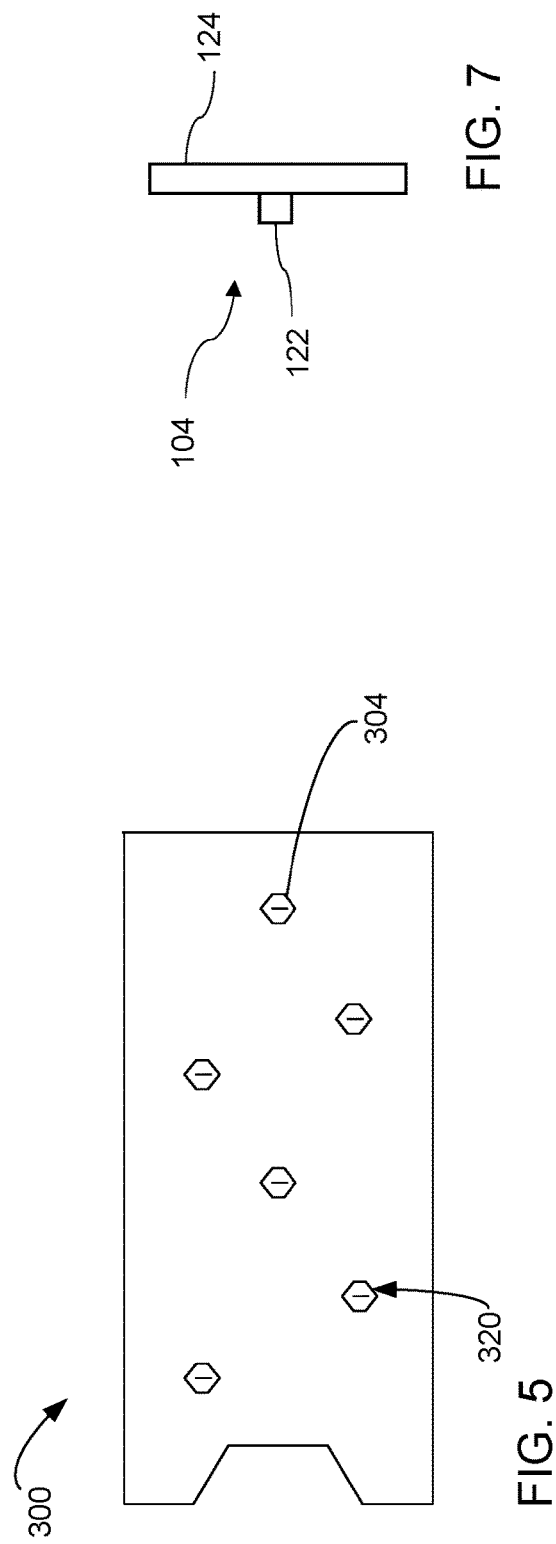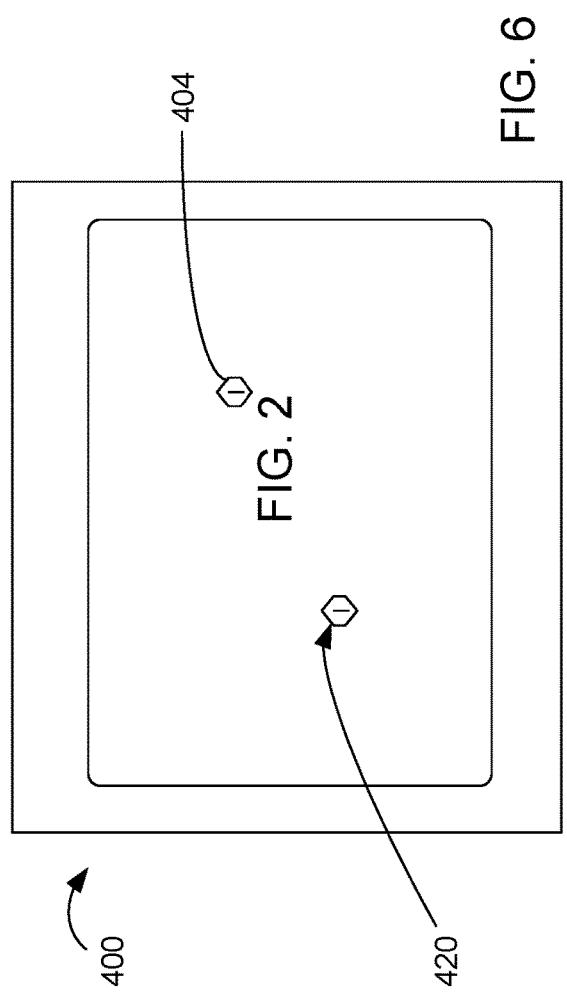

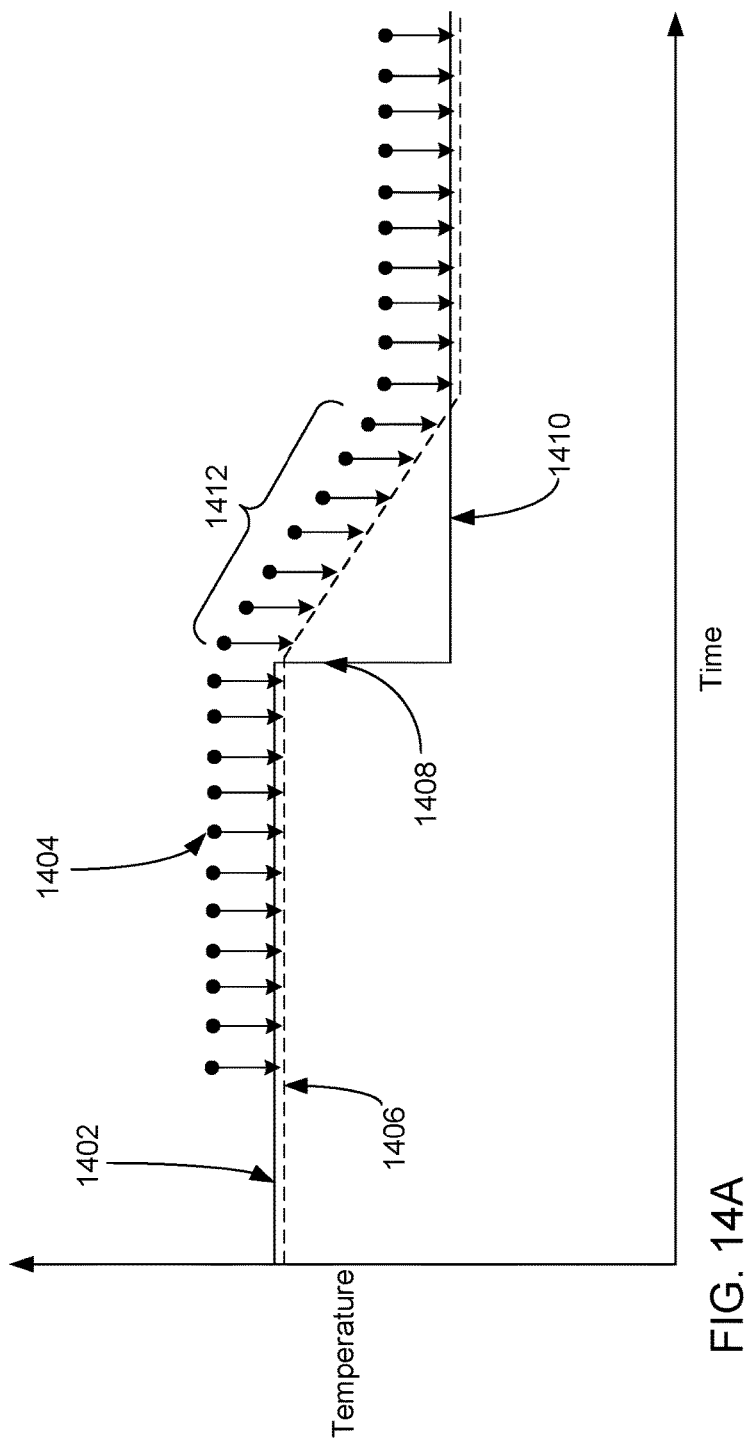
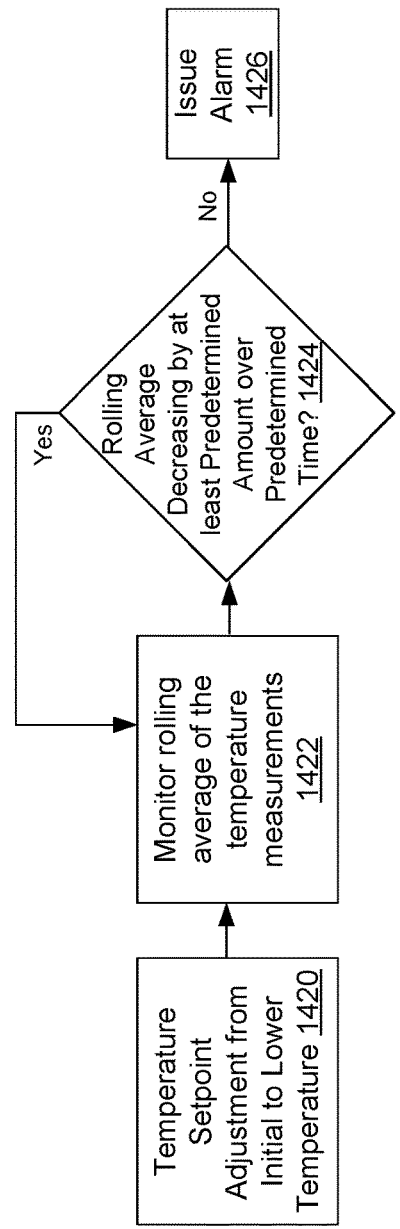
FIG. 14A
FIG. 14B

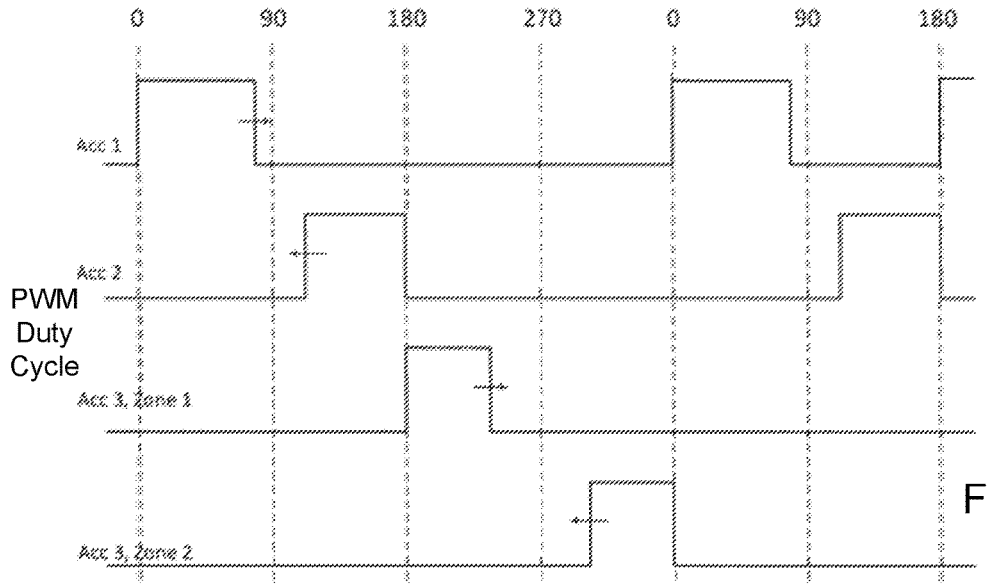
FIG. 18A
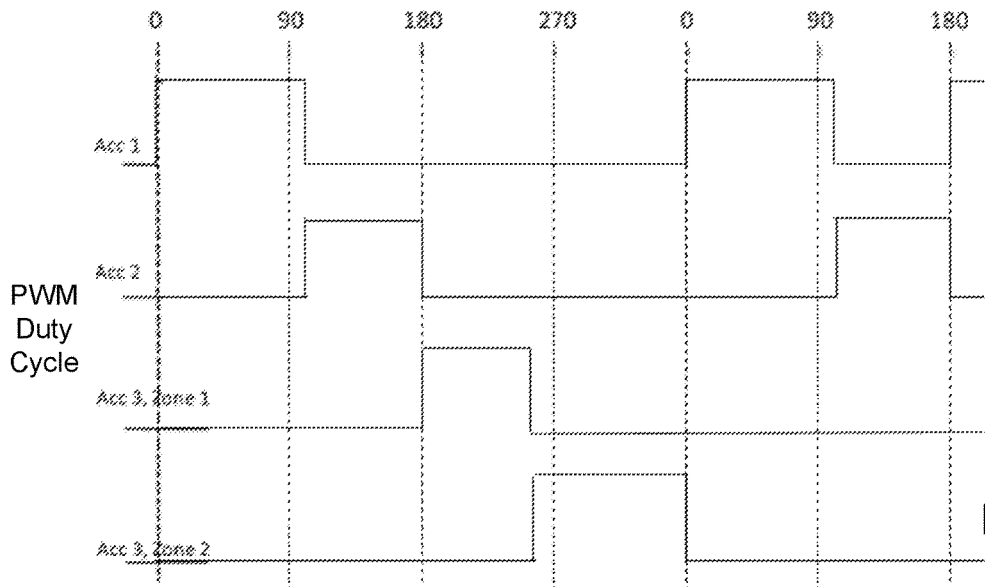
FIG. 18B
FIG. 18C
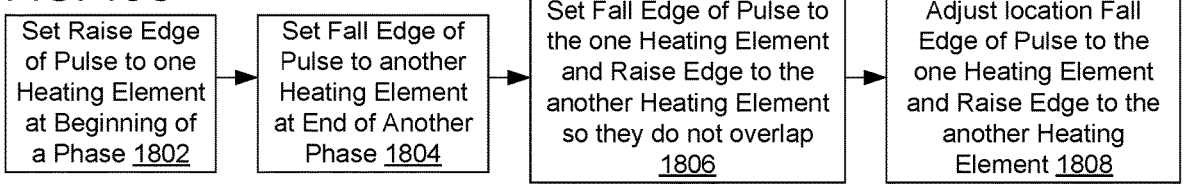

PATIENT WARMING SYSTEM

This application claims priority to U.S. Patent Application No. 62/968,628 filed Jan. 31, 2020. This prior application is incorporated herein by reference.

FIELD OF THE INVENTION

The technology of the present disclosure relates generally to patient warming systems, and more particularly to patient warming systems using electrically conductive heating and the control operation thereof.

BACKGROUND

Patient warming systems are used in various medical applications. For example, surgical patients that undergo surgery and require anesthesia may be warmed using a warming system, as they may be unable to regulate their core body temperature. The patients may be subject to detrimental heat loss if their core body temperature is not able to be maintained.

One conventional method of warming patients includes using forced air convective warming. However, forced air convective warming systems are disadvantageous for several reasons. Using convective warming may transmit lower thermal energy as compared with conductive warming systems, and convective airflow may cause surgical site contamination. Still other disadvantages include less temperature control being available at the patient contact surface, inconsistent temperatures at the surface of the warming device used in the system, excessive noise of the system due to a fan, and the increased surgical site temperature for the surgeons. Forced air convective warming systems also cannot be used during patient preparation due to contamination concerns from the airflow.

Another conventional method of warming patients includes using fluid conductive warming. However, similar to forced air convective warming systems, fluid conductive warming systems have been found to be unable to provide temperature consistency across the warming device for the patient, and can be excessively noisy due to the fan. The temperature at the patient contact surface may also be difficult to control using fluid conductive warming systems. Leaks in the fluid conductive warming system are also a concern. Fluid conductive warming systems may also provide challenges in that a fan on the heat exchanger of the system may build up contaminants that are subsequently blown around, resulting in infection.

Patient warming systems have been implemented in which electrically conductive warming is utilized. However, control of electrically conductive warming systems is also an issue both in terms of temperature consistency and safety.

Also, in general, patient warming systems are limited to a particular type of warming device and/or are designed for a particular application, which places a limitation on the ability to use a given patient warming system in different applications.

SUMMARY OF INVENTION

The present disclosure, therefore, relates to patient warming systems using electrically conductive heating and the control operation thereof.

In accordance with an aspect of the disclosure, a patient warming system includes: a control unit including: an I/O interface including two or more connectors, the two or more connectors having a same configuration; a controller configured to execute a program stored in a memory of the control unit that identifies a warming device plugged into one of the connectors and that controls application of power to the warming device relative to a set temperature and in accordance with the identity of the warming device; warming devices interchangeably coupled to the control unit via the I/O interface, each warming device including: one or more heating elements; one or more temperature sensors; and a connector that is configured to be coupled to any one of the two or more connectors.

In some embodiments, the one or more heating elements are positive temperature coefficient heating elements.

In some embodiments, the program as executed by the controller: monitors a rolling average of temperature measurements from the one or more temperature sensors when the set temperature is changed to a temperature lower than the current measured temperature; and issues an over-temperature alarm or warning if the rolling average decreases by less than a predetermined amount over a predetermined time period.

In some embodiments, the predetermined amount over a predetermined time period is 1° C. per 10 seconds.

In some embodiments, the predetermined amount over a predetermined time period is 1° C. per 1 minute.

In some embodiments, the program as executed by the controller: calculates an area of a temperature curve of the temperature measured by the one or more temperature sensors over the set temperature as a function of time when the measured temperature is above the set temperature; and issues an over-temperature alarm or warning if the calculated area exceeds the predetermined maximum value.

In some embodiments, the predetermined maximum value is in the range of 0.5° C. second to 2° C. second.

In some embodiments, one of the warming devices includes two heating elements and at least two temperature sensors, each of the heating elements having at least one of the temperature sensors associated therewith, and the program as executed by the controller to controls the two heating elements at least in part based on the highest overall temperature sensor reading of the warming device, wherein a percentage of power relative to its maximum power applied to the heating elements of a zone having a highest zone temperature that is less than the highest overall temperature is at most set to a value that is within a predetermined percentage higher than the percentage of power relative to its maximum power applied to the heating elements of the zone having the highest overall temperature.

In some embodiments, the predetermined percentage is up to 75% higher than the percentage of power (relative to its maximum power) applied to the heating element(s) of the zone having the highest overall temperature.

In some embodiments, the one or more temperature sensors of one of the warming devices are spaced apart from an outer layer of the warming device by one or more intervening layers, and the program as executed by the controller compensate for temperature readings of the temperature sensors by applying an offset to the measured temperature.

In some embodiments, the spacing between the temperature sensors and the outer layer of the warming device ranges from 4 millimeters to 20 millimeters.

In some embodiments, the offset is a constant value.

In some embodiments, the offset is varied depending on one or more environmental or thermal load changes.

In some embodiments, the program as executed by the controller budgets application of power among two heating elements via pulse width modulation by: setting the raise edge of a pulse to one of the heating elements at the beginning of a phase; setting the fall edge of a pulse to another heating element at the end of another phase; and setting the location of a fall edge of the pulse to the one heating element and the raise edge of the pulse to the another heating element so they are adjacent one another but do not overlap.

In some embodiments, as set, there is a gap between the location of the fall edge of the pulse to the one heating element and the raise edge of the pulse to the another heating element.

In some embodiments, the program as executed by the controller adjusts one or both of the location of the fall edge of the pulse to the one heating element and the raise edge of the pulse to the another heating element.

In some embodiments, the program is configured to adjust the location of the fall edge of the pulse to the one heating element and the raise edge of the pulse to the another heating element such that the gap is eliminated.

In some embodiments, each warming device includes an identification resistor; and the control unit includes warming device identification circuitry, the warming device identification circuitry configured as a voltage divider including a resistor that is configured to be used in combination with an identification resistor of a warming device to output a non-zero value.

In accordance with another aspect of the disclosure, a patient warming system includes: a warming device including a heating element and one or more temperature sensors; and a control unit including: an I/O interface, the heating element and one or more temperature sensors of the warming device coupled to the control unit via the I/O interface; a controller configured to: execute an application program stored in a memory of the control unit, the application program configured to control application of power to the heating element relative to a set temperature; and execute a monitoring program stored in the memory of the control unit, the monitoring program configured to monitor the temperature of the warming device and cut off application of power to the heating element in the event that an over-temperature condition is detected; control and cutoff circuitry coupled to the I/O interface, the control and cutoff circuitry configured to: apply power to the heating element in response to the application program executed by the controller; cut off power to the heating element in response to the monitoring program as executed by the controller detecting an over-temperature condition; and cut off power to the heating element in response to the control and cutoff circuitry detecting an over-temperature condition, independent of any detection from the monitoring program.

In some embodiments, the control and cutoff circuitry includes two or more independent noise-filter and amplifier circuits, each noise-filter and amplifier circuit configured to filter and amplify respective temperature sensor data input to the control unit from a coupled warming device.

In some embodiments, the output from each of the independent noise-filter and amplifier circuits is split into two different signals.

In some embodiments, the control and cutoff circuitry includes: two or more independent over-temperature comparators coupled to respective ones of the two or more independent noise-filter and amplifier circuits to receive the first portion of the split signal output from the two or more independent noise-filter and amplifier circuits and compare the signal to a cutoff threshold; and a hardware cutoff switch coupled to the two or more independent over-temperature comparators for cutting off power to the I/O interface upon detection of an over-temperature condition.

In some embodiments, the controller is coupled to the two or more independent noise-filter and amplifier circuits to receive the first portion of the split signal output from the two or more independent noise-filter and amplifier circuits.

In some embodiments, the control and cutoff circuitry further includes a software-controlled switch coupled to the controller for cutting off power to the I/O interface upon detection of an over-temperature condition.

In some embodiments, the application program as executed by the controller controls the software-controlled switch to apply power to the warming device.

In some embodiments, the control unit includes multiple instances of the control and cutoff circuitry, each instance of the control and cutoff circuitry coupled to a respective connector of the I/O interface.

In some embodiments, the control and cutoff circuitry includes: a first switch coupling a positive terminal of a power source to the heating element; and a second switch coupling a negative terminal of the power source to the heating element, wherein the application program as executed by the controller controls the opening and closing of both the first switch and the second switch.

In some embodiments, the application program as executed by the controller controls the first switch to open in unison with the second switch, and controls the first switch to close in unison with the second switch.

In accordance with another aspect of the disclosure, a control unit includes: an I/O interface connectable to a warming device; and control and cutoff circuitry coupled to the I/O interface, the control and cutoff circuitry including: two or more independent noise-filter and amplifier circuits, each noise-filter and amplifier circuit configured to filter and amplify respective temperature sensor data input to the control unit, the output from each of the independent noise-filter and amplifier circuits being split into two different signals; two or more independent over-temperature comparators coupled to respective ones of the two or more independent noise-filter and amplifier circuits to receive the first portion of the split signal output from the two or more independent noise-filter and amplifier circuits and compare the signal to a cutoff threshold; a hardware cutoff switch coupled to the two or more independent over-temperature comparators for cutting off power to the I/O interface upon detection of an over-temperature condition; a controller coupled to the two or more independent noise-filter and amplifier circuits to receive the first portion of the split signal output from the two or more independent noise-filter and amplifier circuits, the controller configured to execute an monitoring program stored in a memory of the control unit, the monitoring program configured to monitor the temperature of the warming device and cut off application of power to the heating element in the event that an over-temperature condition is detected; and a software-controlled switch coupled to the controller for cutting off power to the I/O interface upon detection of an over-temperature condition.

In some embodiments, the control unit further includes a NOR gate coupled to the two or more independent over-temperature comparators to receive the comparator outputs, the hardware cutoff switch coupled to the two or more independent over-temperature comparators via the NOR gate.

In some embodiments, the control unit further includes warming device identification circuitry, the warming device identification circuitry configured as a voltage divider including a resistor that is configured to be used in combination with an identification resistor of a warming device to output a non-zero value.

In some embodiments, the warming device identification circuitry is coupled to the controller and the application program as executed by the controller determines the identity of the warming device.

In some embodiments, the control unit further includes an AND gate coupled to the NOR gate to receive the output from the NOR gate, the hardware cutoff switch coupled to the NOR gate via the AND gate, and the warming device identification circuitry is coupled to the AND gate.

In accordance with another aspect of the present disclosure, an application program stored in a memory and executable by a controller of a control unit to budget application of power among two heating elements via pulse width modulation, the application program configured to: set the raise edge of a pulse to one of the heating elements at the beginning of a phase; set the fall edge of a pulse to another heating element at the end of another phase; and set the location of a fall edge of the pulse to the one heating element and the raise edge of the pulse to the another heating element so they are adjacent one another but do not overlap.

In some embodiments, as set, there is a gap between the location of the fall edge of the pulse to the one heating element and the raise edge of the pulse to the another heating element.

In some embodiments, the application program is further configured to adjust the location of the fall edge of the pulse to the one heating element and the raise edge of the pulse to the another heating element.

In some embodiments, the application program is configured to adjust the location of the fall edge of the pulse to the one heating element and the raise edge of the pulse to the another heating element such that the gap is eliminated.

In accordance with another aspect of the disclosure, a patient warming system includes: a warming device including a heating element and one or more temperature sensors; and a control unit including: an I/O interface, the heating element and one or more temperature sensors of the warming device coupled to the control unit via the I/O interface; a controller configured to: execute an application program stored in a memory of the control unit, the application program configured to control application of power to the heating element relative to a set temperature; and a first switch coupling a positive terminal of a power source to the heating element; and a second switch coupling a negative terminal of the power source to the heating element, wherein the application program as executed by the controller controls the opening and closing of both the first switch and the second switch.

In some embodiments, the application program as executed by the controller controls the first switch to open in unison with the second switch, and controls the first switch to close in unison with the second switch.

In accordance with another aspect of the disclosure, a support apparatus, includes: a lateral acting clamp for securing the support apparatus to a vertical support and having a generally C-shaped clamp member, the lateral acting clamp including: a back portion; a first arm extending from the back portion and a second arm extending from the back portion so as to define a channel; a post extending through the first arm and movable in a lateral direction; and one or more hooks for securing the support apparatus to a horizontal support.

In some embodiments, a portion of the first arm constitutes a first hook of the one or more hooks, and a portion of the second arm constitutes a second hook of the one or more hooks.

In some embodiments, the hooks are rigid hooks and have a semi labyrinth opening.

In some embodiments, the one or more hooks are sprung rail hooks secured to the back portion.

In some embodiments, the support apparatus further includes a hinge coupled to the back portion.

In some embodiments, a control unit includes: a housing; and the support apparatus coupled to the housing.

These and further features will be apparent with reference to the following description and attached drawings which set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings. The invention includes all changes, modifications and equivalents coming within the spirit and terms of the claims appended hereto.

Features that are described and/or illustrated with respect to one embodiment may be used in the same way or in a similar way in one or more other embodiments and/or in combination with or instead of the features of the other embodiments.

BRIEF DESCRIPTION OF THE DRAWINGS

The annexed drawings, which are not necessarily to scale, show various aspects of the present disclosure.

FIG. 4A is a perspective view of an exemplary heating element.

FIG. 4B is a schematic drawing showing an exploded view of an exemplary layer arrangement of the heating element of FIG. 4A.

FIG. 5 is a schematic top view of an exemplary underbody pad.

FIG. 6 is a schematic bottom view of an exemplary over-body blanket.

FIG. 7 is a schematic side view of an exemplary temperature sensor.

FIG. 14A is an exemplary temperature profile of a measured temperature over time relative to a temperature setpoint change.

FIG. 14B is a flowchart in accordance with FIG. 14A.

FIGS. 18A and 18B are graphs showing exemplary divisions of power among warming devices per duty cycle.

FIG. 18C is a flowchart in accordance with FIGS. 18A and 18B.

DETAILED DESCRIPTION

Figure 1:
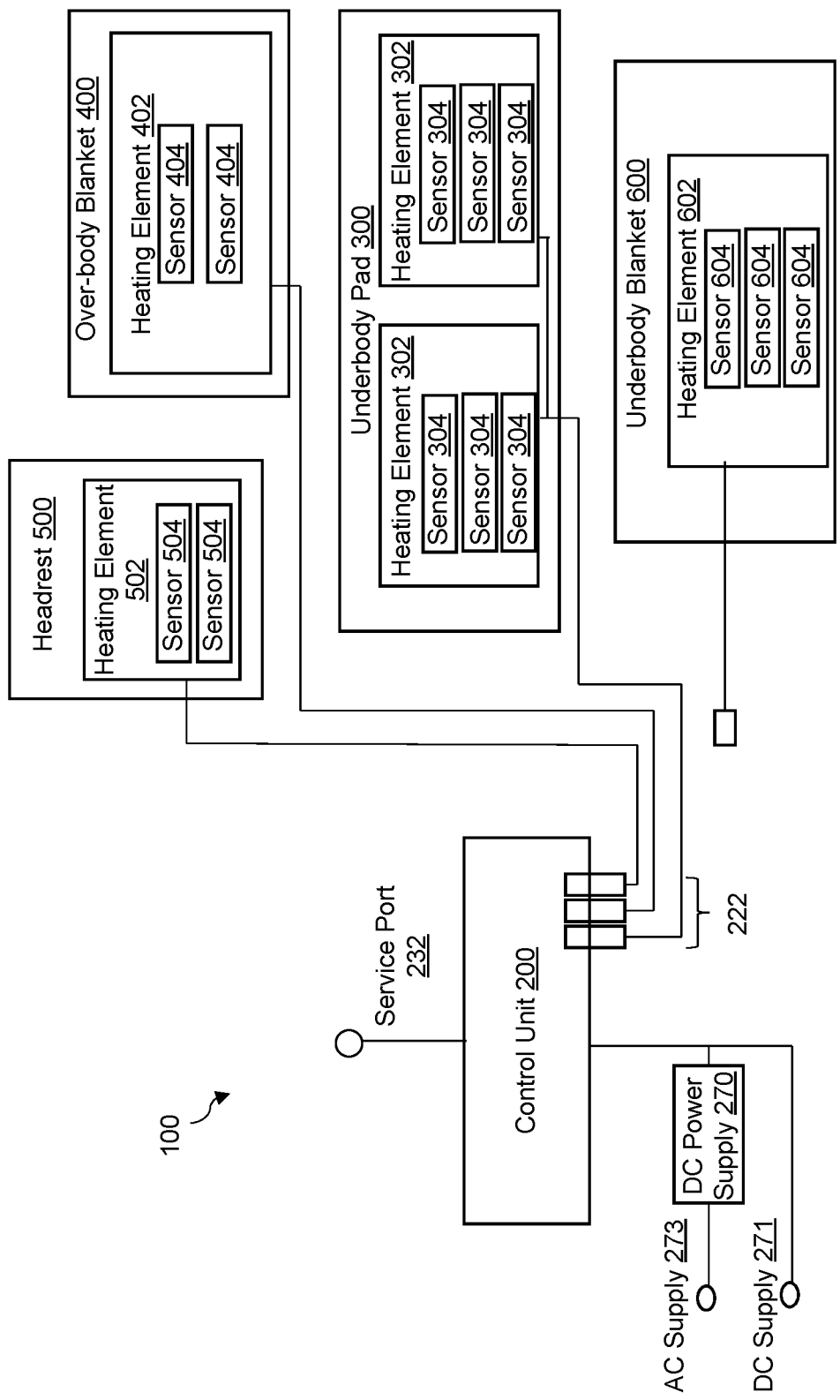
FIG. 1 is a schematic block diagram of an exemplary patient warming system.

For the purpose of promoting an understanding of the principles of the present disclosure, reference will now be made to the embodiments illustrated in the drawings and specific language will be used to describe the same. It will nevertheless be understood that no limitation of the scope of the present disclosure is thereby intended. Any alterations and further modifications of the described embodiments, and any further applications of the principles of the present disclosure as described herein, are contemplated as would normally occur to one skilled in the art to which the present disclosure relates.

With reference to FIG. 1, an exemplary patient warming system is shown at 100. The patient warming system is a modular system, and includes a control unit 200 that may be electrically coupled to one or more warming devices. The one or more warming devices may be controlled by the control unit 200 to produce heat using one or more electrically resistive heating elements, and may provide conductive heat transfer from the warming device to the patient.

In the example shown, the control unit 200 is electrically coupled to each of an underbody pad 300 (e.g., torso pad), over-body blanket 400, and headrest 500. In other embodiments, the control unit 200 may have more or fewer warming devices electrically coupled thereto. Other exemplary warming devices including one or more electrically resistive heating elements that may be coupled to the control unit 200 and used in connection with the patient warming system 100 include an under-body blanket 600 (shown in FIG. 1 as being in an uncoupled state), head pad (not shown), foot pad (not shown), and the like. A warming device used in connection with the patient warming system can be reusable or disposable (e.g., one-time use). In some embodiments, the warming devices used in the patient warming system are all reusable. In other embodiments, the warming devices used in the patient warming system are all disposable (e.g., one-time use). In other embodiments, the warming devices used in the patient warming system are a combination of reusable and disposable (e.g., one-time use) warming devices.

The patient warming system 100 is modular in that any one of (or combination of) the warming devices may be coupled to the control unit 200 (e.g., via the I/O interface 222) and operated to provide conductive heat transfer to the patient. A coupled warming device may be uncoupled from the control unit 200, and one or more other warming devices may be electrically coupled to the control unit 200 in its place. For example, FIG. 1 shows an underbody pad 300, over-body blanket 400, and headrest 500 coupled to the control unit 200 via the I/O interface, and an underbody blanket 600 uncoupled from the control unit 200. One of the warming devices (e.g., the underbody pad 300) may be uncoupled from the control unit 200 and the underbody blanket 600 may be coupled to the control unit in its place.

The control unit 200 may support individual and/or concurrent operation of multiple warming devices. In some embodiments, concurrent operation may be performed with the coupled warming devices being controlled based on one or more common parameters (e.g., set point, on time, off time, etc.). In other embodiments, concurrent operation may be performed with the coupled warming devices being controlled independently of one another. Adding, removing, or swapping a warming device may have no impact on the control of other warming devices.

Figure 2:
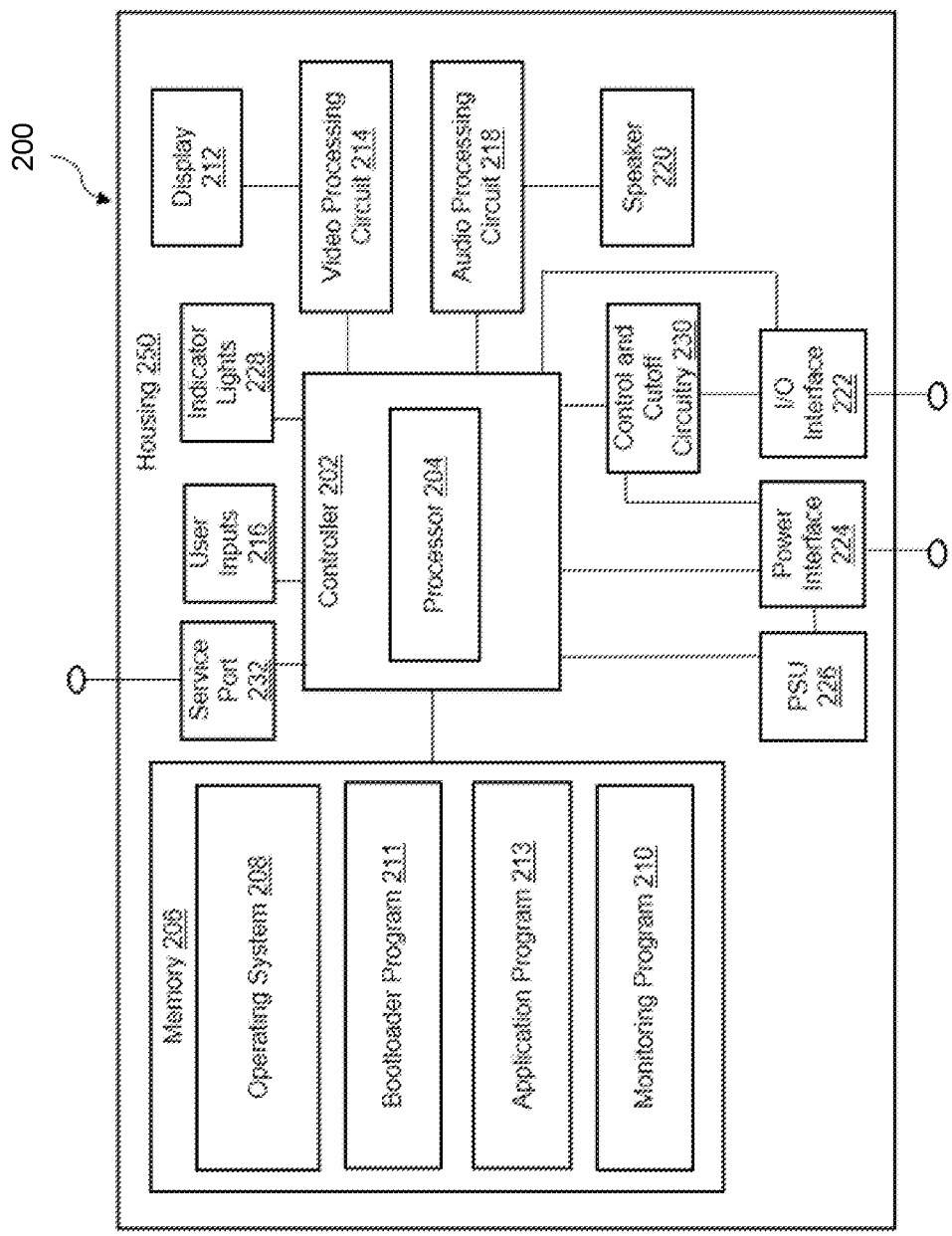
FIG. 2 is a schematic block diagram of an exemplary control unit.

With additional reference to FIG. 2, the control unit 200 may include a controller 202 that is configured to carry out overall control of the functions and operations of the control unit 200. The controller 202 may include a processor 204, such as a central processing unit (CPU), microcontroller, or microprocessor. The processor 204 executes code stored in a memory (not shown) within the controller 202 and/or in a separate memory, such as the memory 206, in order to carry out operation of the control unit 200 and patient warming system 100. For example, the processor 204 may execute an operating system 208, monitoring program 210, bootloader program 211, application program 213, and/or other programs. In the example shown, the operating system 208, monitoring program 210, bootloader program 211, and application program 213 are stored on the memory 206. In other examples (not shown), the operating system 208, monitoring program 210, bootloader program 211, and/or application program 213 may be stored in a memory within the controller 202.

The operating system 208 may be embodied in the form of executable logic routines (e.g., lines of code, software programs, etc.) that are stored on a non-transitory computer readable medium (e.g., the memory 206) of the control unit 200 and are executed by the controller 202 (e.g., using the processor 204). Furthermore, monitoring program 210, bootloader program 211, and/or application program 213 may be a stand-alone software program or form a part of a software program that carries out additional tasks related to the control unit 200 (e.g., a part of the operating system 208, a combination of the monitoring program 210 and the application program 213, etc.).

The operating system 208 may be executed by the processor 204 to control the allocation and usage of resources in the control unit 200, as well as provide basic user interface features. Specifically, the operating system 208 may control the allocation and usage of the memory 206, the processing time of the processor 204 dedicated to various applications being executed by the processor 204, as well as performing other functionality. In this manner, the operating system 208 may serve as the foundation on which programs, such as the application program 213, bootloader program 211, and/or monitoring program 210 depend, as is generally known by those with ordinary skill in the art. The operating system 208 also may control aspects of the user interface environment presented to a user, such as features of the overall graphical user interface (GUI) for the control unit 200.

The application program 213 may be configured to control the temperature of all of the connected warming devices. The application program 213 may control application of power to the heating element(s) of a given connected warming device in accordance with the temperature setpoint and the temperature readings from a temperature sensor of the warming device. The application program may divide power to respective heating elements of device heating zones in a budgeted manner that avoids exceeding the total power budget that the control unit can collectively deliver to the connected warming devices at any given time. The application program 213 may also determine the identity of a warming device when plugged in, and configure limits, tuning parameters, and/or the GUI display appropriately for the connected device. While the application program 213 is described herein as performing each of the above operations, it will be appreciated that the application program 213 may include one or more modules, each module configured to perform one or more dedicated functions. Additional details and operation of the application program 213 will be described in greater detail below.

The bootloader program 211 may be configured to launch the application program and/or the monitoring program 210. The bootloader program 211 may also be configured to update the application program and/or the monitoring program 210. The bootloader program 211 may also be configured to perform self-tests at power-on of the control unit. While the bootloader program 211 is described herein as performing each of the above operations, it will be appreciated that the bootloader program 211 may include one or more modules, each module configured to perform one or more dedicated functions. Additional details and operation of the bootloader program 211 will be described in greater detail below.

The monitoring program 210 may be configured to monitor temperature of the coupled warming devices and control application of power to the heating element(s) of a given connected warming device by effecting the cutoff of the supply of power to the warming devices in the event that an overtemperature condition and/or fault is detected. It will be appreciated that an overtemperature condition is a state in which a temperature read by a temperature sensor of the warming device is at or above a predetermined maximum temperature, said predetermined maximum temperature being independent of the set temperature of the device. The control of the application of power to the heating element(s) of a given connected warming device in this manner may operate as a software-based, redundant overtemperature control that may in some embodiments be used in addition to the separate hardware-based overtemperature control, described below. The monitoring program 210 may also perform self-tests at power-on, when a device is plugged in, and/or during normal operation, to detect any hardware failures. While the monitoring program 210 is described herein as performing each of the above operations, it will be appreciated that the monitoring program 210 may include one or more modules, each module configured to perform one or more dedicated functions. Additional details and operation of the monitoring program 210 will be described in greater detail below.

It will also be appreciated that while the application program 213 and the monitoring program 210 are described herein as separate programs, in some embodiments, the application program 213 and the monitoring program 210 may be a single program. For example, the monitoring program 210 be included as part of the application program 213. In other embodiments, one or more modules/functions of the monitoring program 210 be included as part of the application program 213.

The memory 206 may be, for example, one or more of a buffer, a flash memory, a hard drive, a removable media, a volatile memory, a non-volatile memory, a random access memory (RAM), or other suitable device. In a typical arrangement, the memory 206 may include a non-volatile memory for long term data storage and a volatile memory that functions as system memory for the controller 202. The memory 206 may exchange data with the controller 202 over a data bus. Accompanying control lines and an address bus between the memory 206 and the controller 202 also may be present. The memory 206 is considered a non-transitory computer readable medium.

The control unit 200 may also include control and cutoff circuitry 230. The control and cutoff circuitry 230 may be used to monitor temperature of the warming devices and control the supply of power to the warming devices in the event that an overtemperature situation and/or fault is detected. The control and cutoff circuitry 230 may, in conjunction with the monitoring program 210, provide a combination of software and hardware approaches to monitor and detect an overtemperature situation and/or fault. The control and cutoff circuitry 230 may also be used to provide operating power (e.g., pulse width modulation (PWM) power) to connected warming devices. Additional details and operation of the control and cutoff circuitry 230 will be described in greater detail below.

The control and cutoff circuitry 230 is shown in FIG. 1 as separate from the controller 202. In other embodiments, the control and cutoff circuitry 230 may be a part of controller 202.

With continued reference to FIG. 2, the control unit 200 may include a display 212. The display 212 displays information to a user such as operating state, temperature, set points, warnings, various menus, etc., that enable the user to utilize the various features of the control unit 200 and patient warming system 100. The display 212 also may be used to visually display content received by the controller 202 and/or retrieved from a memory 206 of the control unit 200. The display 212 may be used to present images, video and other graphics to the user. The display may be a lighted display. In some embodiments, the display 212 is a backlit liquid-crystal display (LCD). The LCD may be backlit using one or more suitable light sources (e.g., a light emitting diode (LED), cold cathode fluorescent (CCFL), etc.). In other embodiments, the display 212 is an organic light-emitting diode (OLED) display.

The display 212 may be coupled to the controller 202 by a video processing circuit 214 that converts image and/or video data to an image and/or video signal used to drive the display 212. The video processing circuit 214 may include any appropriate buffers, decoders, video data processors and so forth. The image and/or video data may be generated by the controller 202, retrieved from an image and/or video file that is stored in the memory 206.

The control unit 200 may include one or more user inputs 216 for receiving user input for controlling operation of the control unit 200. Exemplary user inputs 216 include, but are not limited to, a touch input that overlays the display 214 for touch screen functionality, one or more buttons, and so forth.

The control unit 200 may further include a audio processing circuit 218 for processing audio signals. Coupled to the audio processing circuit 218 is a speaker 220 that enables a user to hear sounds generated in connection with other functions of the control unit 200. The audio processing circuit 218 is coupled to the controller 202 so as to carry out overall operation. Audio data may be passed from the controller 202 to the audio processing circuit 218 for playback to the user. The audio processing circuit 218 may include any appropriate buffers, decoders, encoders, amplifiers and so forth.

The control unit 200 may further include one or more indicator lights 228. The one or more indicator lights may be selectively illuminated by the controller 202. Illumination of the one or more indicator lights may be in accordance with overall operation, and may be used to indicate to a user the state, status, and/or condition of the system. For example, an indicator lights may be used to indicate one or more of an operation mode, a warning, connected state of a warming device, etc.

The control unit 200 may further include one or more input/output (I/O) interface(s) 222. The I/O interface(s) 222 may be in the form of one or more electrical connectors and may connect the control unit 200 to one or more warming devices (e.g., underbody pad 300, over-body blanket 400, headrest 500, and/or under-body blanket 600). In some embodiments, the one or more electrical connectors include one or more universal sockets that can each be used to mate with a plug (connector) of any of the warming devices of the patient warming system 100. The one or more electrically connectors may have the same configuration. In other embodiments, the one or more electrical connectors include one or more sockets that can each be used to mate with a plug of a warming device of a first subset of the warming devices of the patient warming system; and one or more other sockets that can each be used to mate with a plug of a warming device of a second subset of the warming devices of the patient warming system. For example, the control unit 200 may include one socket that can be used to mate with a plug of an underbody pad or an underbody blanket; and two other sockets, each of which can be used to mate with a plug of a headrest or over-body blanket. The one or more electrically connectors may have the same configuration or different respective configurations.

The control unit 200 may further include a service port 232. The service port may be any suitable port (e.g., USB) for uploading system data and/or updates to the control unit. In some embodiments, the service port 232 may be used to upload an update to, or a new version of the application program 213 and/or monitoring program 210, and the bootloader program 211 may use this data to conduct the update.

Operating power may be received from an external power source via a power interface 224. The control unit 200 may in some embodiments include a power supply unit (PSU) 226 (e.g., a battery), and power to charge the power supply 226 may be received via the power interface 224. The power supply 226 may supply power to operate the control unit 200 and/or supply power to the one or more connected warming devices in the absence of an external power source. The control unit may apply any suitable amount of power to the heating elements of the connected warming devices. In some embodiments, the control unit applies at least 24V power to the heating elements of the connected warming devices. In some embodiments, the control unit applies at least 36V power to the heating elements of the connected warming devices. In other embodiments, the control unit applies 48V power to the heating elements of the connected warming devices. In some embodiments, the control unit may apply power in a range from any one of the above-described values to 100V power. It will be appreciated that the amount of power may be selected and applied in accordance with the power/operating parameters and requirements of the warming device. The control unit may also in some embodiments apply different voltages to different connected warming devices depending on their respective power/operating parameters and requirements.

With reference to FIG. 1, the external power source may be a DC supply 271 or an AC supply 273. A DC power supply 270 may be used to convert AC power to DC power.

Figure 3:
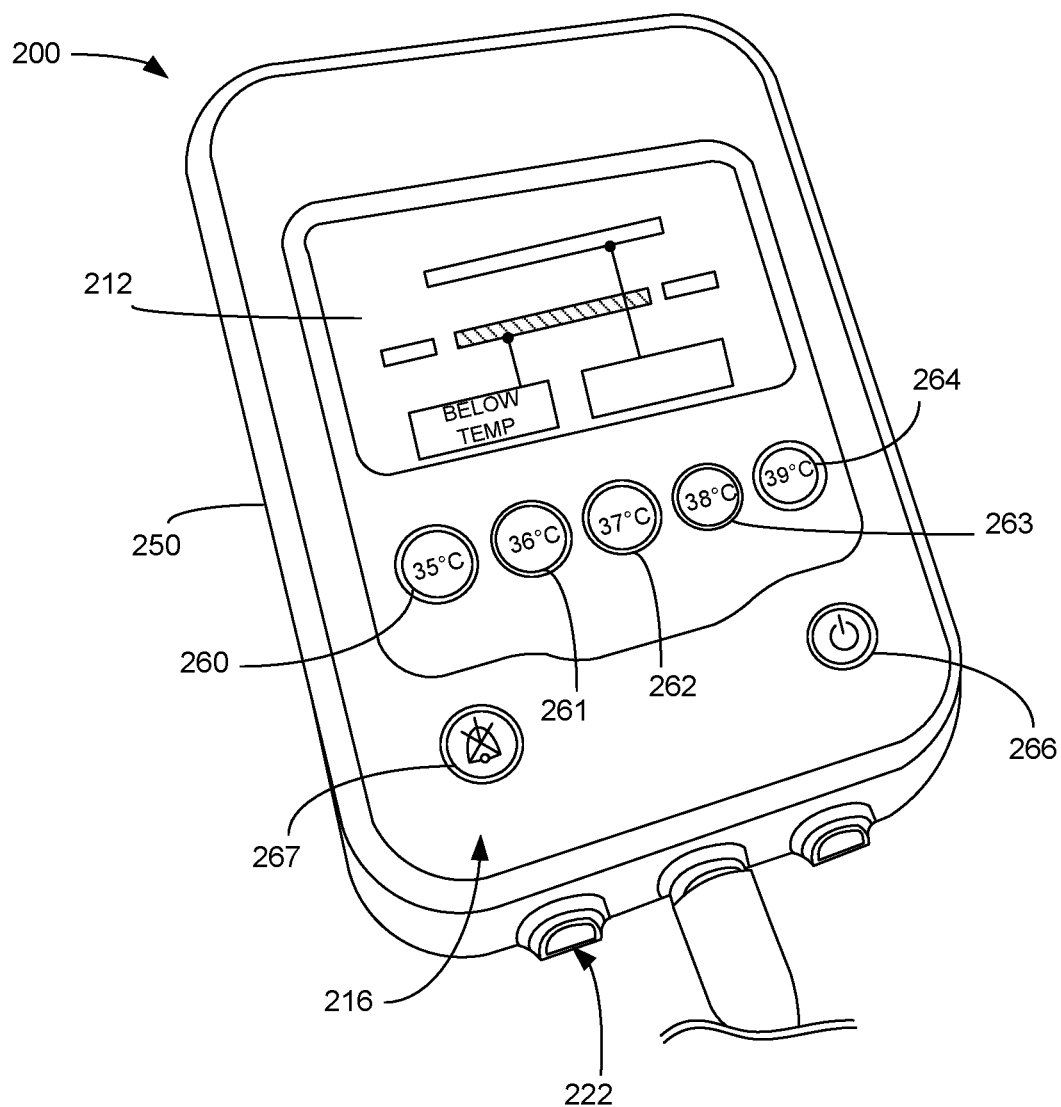
FIG. 3 is a front perspective view of an exemplary control unit.

The control unit includes a housing 250 for housing the components of the control unit 200. FIG. 3 shows a perspective view of an exemplary housing 250 of a control unit 200. As shown, the control unit 200 includes a display 212 retained by the housing. In the example, the display 212 shows status information of connected warming devices. User inputs are retained by the housing for use by a user. Specifically, temperature control buttons 260, 261, 262, 263, 264 are provided adjacent the display for selecting a desired temperature for a given (or for all of the) connected warming devices, and a power button 266 and an alarm cancel button 267 are also provided. I/O interfaces 222 are provided for connecting the warming devices.

As exemplified in FIG. 1, the patient warming system 100 may include one or more warming devices electrically coupled to the control unit 200. Each of the warming devices respectively includes one or more heating elements. The exemplary underbody pad 300 shown in FIG. 1 includes two heating elements 302, and each of the exemplary over-body blanket 400, headrest 500, and under-body blanket 600 shown in FIG. 1 respectively include one heating element 402, 502, 602. It will be appreciated that the number of heating elements for a given warming device is not limited to the particular number depicted in the example shown in FIG. 1, and in other embodiments, each respective warming device may include any suitable number of heating elements.

In some embodiments, the heating elements used in the patient warming system are positive temperature coefficient (PTC) heating elements. FIGS. 4A and 4B show an exemplary PTC heating element 102. The PTC heating element 102 may be a laminated structure that includes an electrically insulating layer 105, an electrically conductive layer 106, and a resistive layer 116. The electrically insulating layer 105 may constitute a substrate layer of the lamination and is formed of a suitable electrically insulating and flexible material. Examples of suitable materials for the electrically insulating layer 105 include polyethylene, polyethylene terephthalate (PET), thermoplastic polyurethane (PU), or polyamide.

The electrically conductive layer 106 and may be formed of a screen-printed conductive ink. In some embodiments, the screen-printed conductive ink is a flexible polymeric ink. In other embodiments, the electrically conductive layer 106 is a metal or metal alloy (e.g., silver, gold, platinum, etc.). The electrically conductive layer 106 may be applied to the electrically insulating layer 105 by screen printing or any other suitable method, such as deposition, digital printing, inkjet printing, flexographic printing, or gravure printing. The electrically conductive layer 106 includes electrical buses 108, 110 spaced relative to each other, and fingers 112, 114 that extend from the respective bus 108, 110 toward the other bus. The arrangement of the busses 108, 110 and fingers 112, 114 is merely exemplary and other arrangements may be suitable.

The fingers 112, 114 and busses 108, 110 are electrically connected by a resistive layer 116. The resistive layer 116 is configured to provide the self-regulating characteristic for the heating element 102. The resistive layer 116 is formed adjacent the electrically conductive layer 106 and is formed of a positive thermal coefficient (PTC) material, such as a PTC ink. The PTC material may be printed over the electrically conductive layer 106. The PTC material has a higher electrical resistance than the electrically conductive layer 106. The PTC material may be produced to achieve a predetermined threshold temperature at which the heating element 102 is self-regulating. For example, a temperature between 45° C. and 65° C. may be the threshold temperature for a particular application. In an exemplary application, the threshold temperature may be around 55° C.

In operation, the self-regulating characteristic for the heating element 102 is provided by way of the PTC effect that occurs when the heating element 102 is heated. The resistive layer 116 is configured to generate heat when voltage is applied across the busses 108, 110 via terminals that are provided for the busses. In some embodiments, the PTC material may include a network in which one or more electrically conductive materials (e.g., carbon or one or more suitable conductive material) are dispersed in a polymer or other suitable carrier material. As the PTC material is heated, thermal expansion causes the PTC material to expand such that respective distances between conductive materials in the network increase, thereby increasing electrical resistance of the PTC material at higher temperatures. The resistance curve of such PTC materials may be parabolic in shape. In other embodiments, as the PTC material is heated, the temperature of the material rises until it exceeds a phase transformation temperature and the resistance of the heating element 102 rapidly increases. In such embodiments, the resistance curve of the PTC material may be more hyperbolic in shape The PTC effect may cause the heating element to draw more current when at lower temperatures, causing the warming devices to reach the setpoint temperature more quickly. As temperature of the PTC material increases, its resistance also increases but. When the threshold temperature is reached, the heating element 102 may be configured to throttle heat output when the threshold temperature of the PTC material is reached (due to the high resistance state of the PTC material at that temperature), and will do so as long as the PTC material is at the threshold temperature. When the temperature of the PTC material is lowered, the resistance of the PTC material will decrease (e.g., due to the PTC material contracting and/or undergoing a reverse phase transformation). The PTC material therefore provides the heating element with a "self-regulating" temperature effect to limit the heating element from reaching a temperature above a predetermined value. The self-regulating temperature effect also helps to improve the thermal uniformity of the heating element.

With continued reference to FIG. 4B, the heating element may in some embodiments further include an additional insulation layer 117 adjacent the resistive layer 116. In some embodiments, a fabric layer 119 may also be provided adjacent the additional insulating layer 117 such that the additional insulating layer 117 is disposed between the fabric layer 119 and the resistive layer 116. In other embodiments, one or both of the additional insulation layer 117 and the fabric layer 119 may be omitted.

It will be appreciated that while the heating elements in the patient warming system are described as being embodied as PTC heating elements, in other embodiments one or more of the heating elements used in the patient warming system may be a heating element other than a PTC heating element. Other non-limiting examples include traditional temperature coefficient heating elements (e.g., conductive inks, perforated carbon veil, carbon impregnated fabrics, etc.), negative temperature coefficient heating elements, or any other suitable heating element that may be used for electrically conductive warming.

With continued reference to FIG. 1, control of a warming device may be conducted using one or more temperature sensors of the warming device. The temperature sensors may be used in both control the temperature of the warming device, and in triggering the safety (overtemperature) cut off. One or more temperature sensors of the warming device may be used in the control of a heating zone of the warming device. In some embodiments, one heating element is associated with a given heating zone and the one or more temperature sensors associated with that given heating zone may be used in the control of that heating element. In other embodiments, more than one (e.g., 2, 3, 4, etc.) heating element is associated with a given heating zone and the one or more temperature sensors associated with that given heating zone (and with the respective heating elements therein) may be used in the control of all of the heating elements in that given zone. In some embodiments, a warming device may have a single heating zone. In other embodiments, a warming device may have more than one heating zone. In some implementations of the more than one heating zone embodiments of the warming device, the heating zones may each have the same number of heating elements. In some implementations of the more than one heating zone embodiments of the warming device, the heating zones may have different respective numbers of heating elements. In the exemplary embodiment shown in FIG. 1, each of the warming devices are embodied as having one heating element associated with a respective heating zone. The exemplary underbody pad 300 shown in FIG. 1 includes three sensors 304 associated with each heating element 302 (zone), each of the over-body blanket 400 and headrest 500 shown in FIG. 1 includes two sensors 404, 504 associated with the heating element 402, 502 (zone) respectively, and under-body blanket 600 shown in FIG. 1 includes three sensors 604 associated with the heating element 602. It will be appreciated that reference to a temperature sensor being associated with a heating element also may constitute reference to the temperature sensor being associated with a heating zone. It will also be appreciated that the number of temperature sensors for a given warming device, and the number of temperature sensors associated with a given heating element, is not limited to the particular number depicted in the example shown in FIG. 1. In other embodiments, each respective warming device may include any suitable number of temperature sensors.

FIG. 5 shows an exemplary underbody pad 300 embodied as a torso pad, and FIG. 6 shows an exemplary over-body blanket 400. As shown, each of the warming devices includes an arrangement of temperature sensors 304, 404. The temperature sensors are arranged such at least one of the sensors overlays a patient or the patient is placed on top of at least one of the sensors when the warming device is in use. The multiple temperature sensors in a warming device may allow for flexible positioning of the patient with respect to the warming device, and may accommodate a variety of patient body types and positions.

A schematic side view of an exemplary temperature sensor 104 is shown in FIG. 7. The exemplary temperature sensor 104 may be representative of any one of the temperature sensors 304, 404, 504, 604 included in a warming device. The temperature sensor 104 includes one or more thermistors 122 and a heat spreader 124. The heat spreader 124 may be cut as a four-sided pyrolytic graphite sheet structure. The graphite sheet structure may in some embodiments include a graphite material laminated to a film, such as a PET film. In an exemplary embodiment, the graphite sheet structure may have a thermal conductivity in an x-y plane that is around 1,900 watts per meter-Kelvin and a thermal conductivity in a z plane that is around 15 watts per meter-Kelvin. Other materials may be suitable for the heat spreader 124. The heat spreader may allow an average temperature to be provided in a predetermined area such that hot or cold spots over the heating element are reduced or eliminated. The heat spreader 124 may be coupled to the one or more thermistors 122 by an adhesive, such as an acrylic adhesive. Adhesive may adhere the heat spreader 124 to a layer in the warming device. In other embodiments, the heat spreader may be omitted from the temperature sensor.

Figure 8:
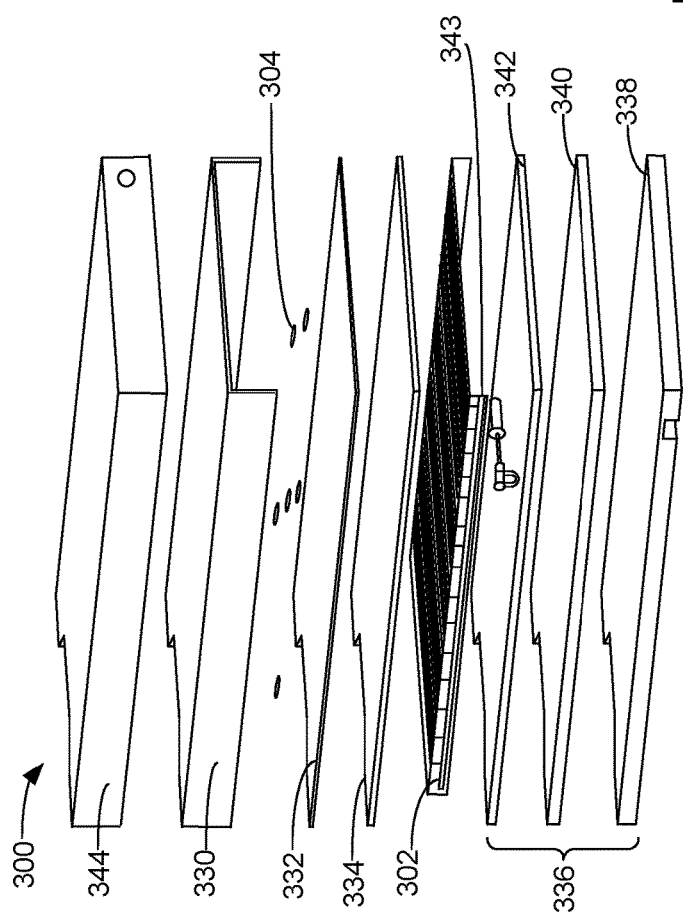
FIG. 8 is an exploded perspective schematic view of the exemplary underbody pad of FIG. 5.
Figure 9:
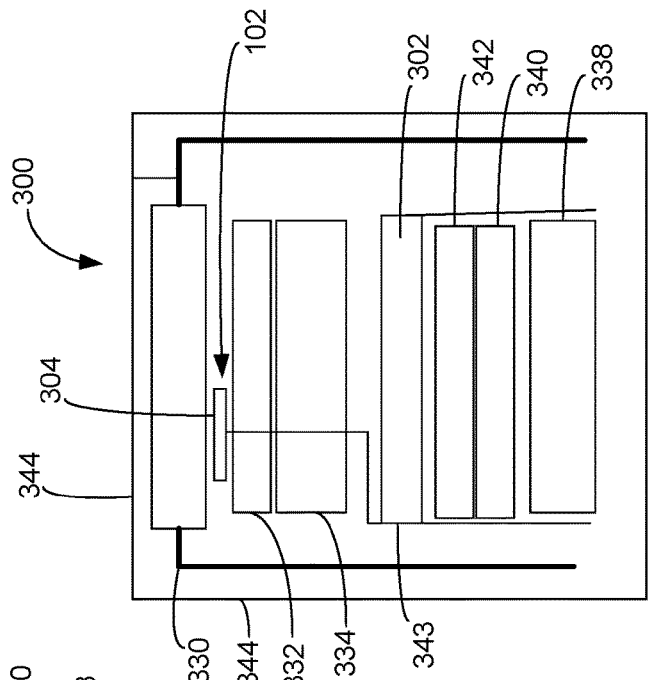
FIG. 9 is a schematic side view of the exemplary underbody pad of FIG. 5.

Referring now to FIGS. 8 and 9, a layer structure of an exemplary underbody pad is shown at 300. The layers include a spacer layer 330, temperature sensors 304, viscoelastic foam layer 332, spacer layer 334, heating element 302, and base foam layer arrangement 336. The temperature sensors 304 are disposed between the spacer layer 334 and the viscoelastic foam layer 332. The base foam layer arrangement 336 may include a high density foam layer 338 that forms the bottom layer, a medium density foam layer 340 arranged adjacent the high density foam layer 338, and a viscoelastic foam layer 342 formed of a viscoelastic material and arranged adjacent the medium density foam layer 338 opposite the high density foam layer 338. The foam layers 336, 338, 340 may form a subassembly that that is adjacent a side of the heating element 302. The viscoelastic foam layer 332 and the spacer layer 334 may form a subassembly that is arranged adjacent a side of the heating element 302 opposite the base foam layer arrangement 336. As shown in FIGS. 8 and 9, the heating element 302 may wrap down around the edges of the base foam layer arrangement 336. A wire harness assembly 343 is used in connecting the temperature sensors 304 and the control unit 200, and also connects the voltage supply to the heating element 302. A cover 344 encloses the layers and may prevent liquid ingress in the underbody pad 300.

Figure 10:
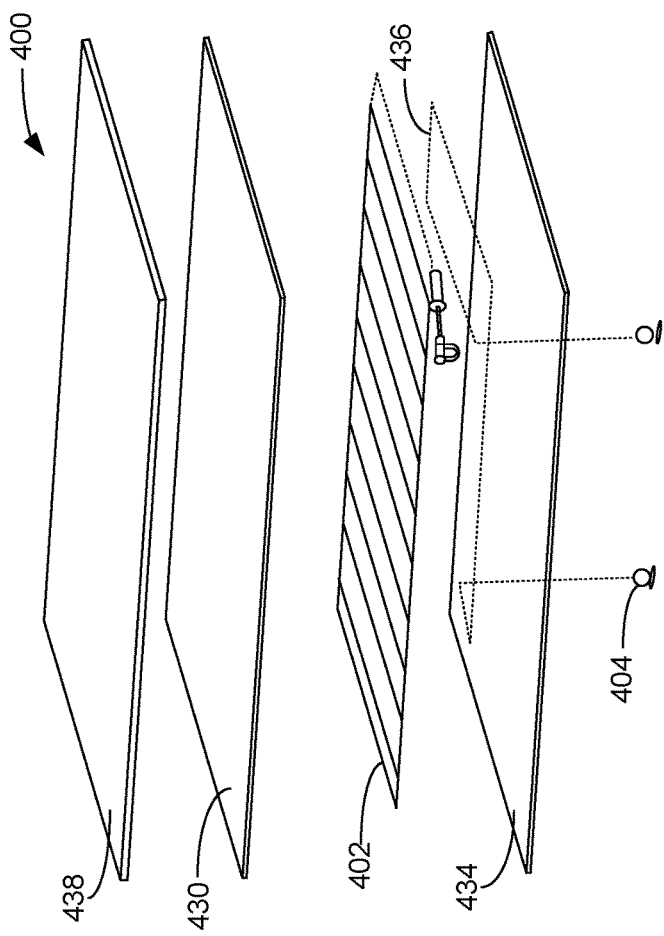
FIG. 10 is an exploded perspective schematic view of the exemplary over-body blanket of FIG. 6.
Figure 11:
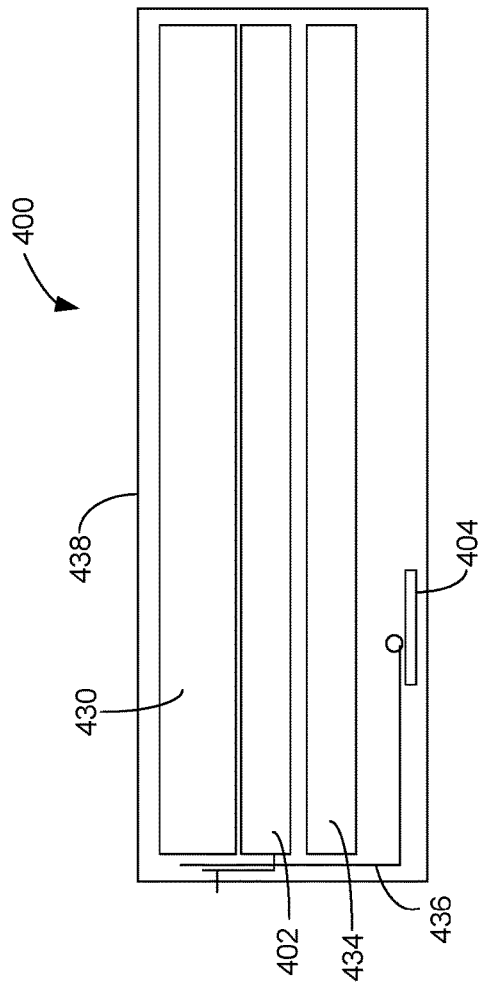
FIG. 11 is a schematic side view of the exemplary over-body blanket of FIG. 6.

Referring now to FIGS. 10 and 11, a layer structure of an exemplary over-body blanket 400 is shown. The layers include viscoelastic foam layer 430, heating element 402, spacer layer 434, temperature sensors 404, and wire harness assembly 436. A cover 438 encloses the layers and may prevent liquid ingress in the blanket. The temperature sensors 404 are disposed between the spacer layer 434 and the cover 438. The wire harness assembly 436 is used in connecting the temperature sensors 404 to the control unit 200, and also connects the voltage supply to the heating element 402. The viscoelastic foam layer 430 provides an insulation layer for directing heat toward the patient and increasing a conformability of the blanket 400.

The patient warming system must reliably control the temperature of warming devices to prevent possible thermal injuries to a patient. As described above, patient warming systems includes a combination of software and hardware approaches to ensure reliability and safety. Both the monitoring program (via execution by the controller) and the hardware within the control and cutoff circuitry may monitor temperature of the warming devices and control the supply of power to the warming devices in the event that an over-temperature situation and/or fault is detected.

Figure 12:
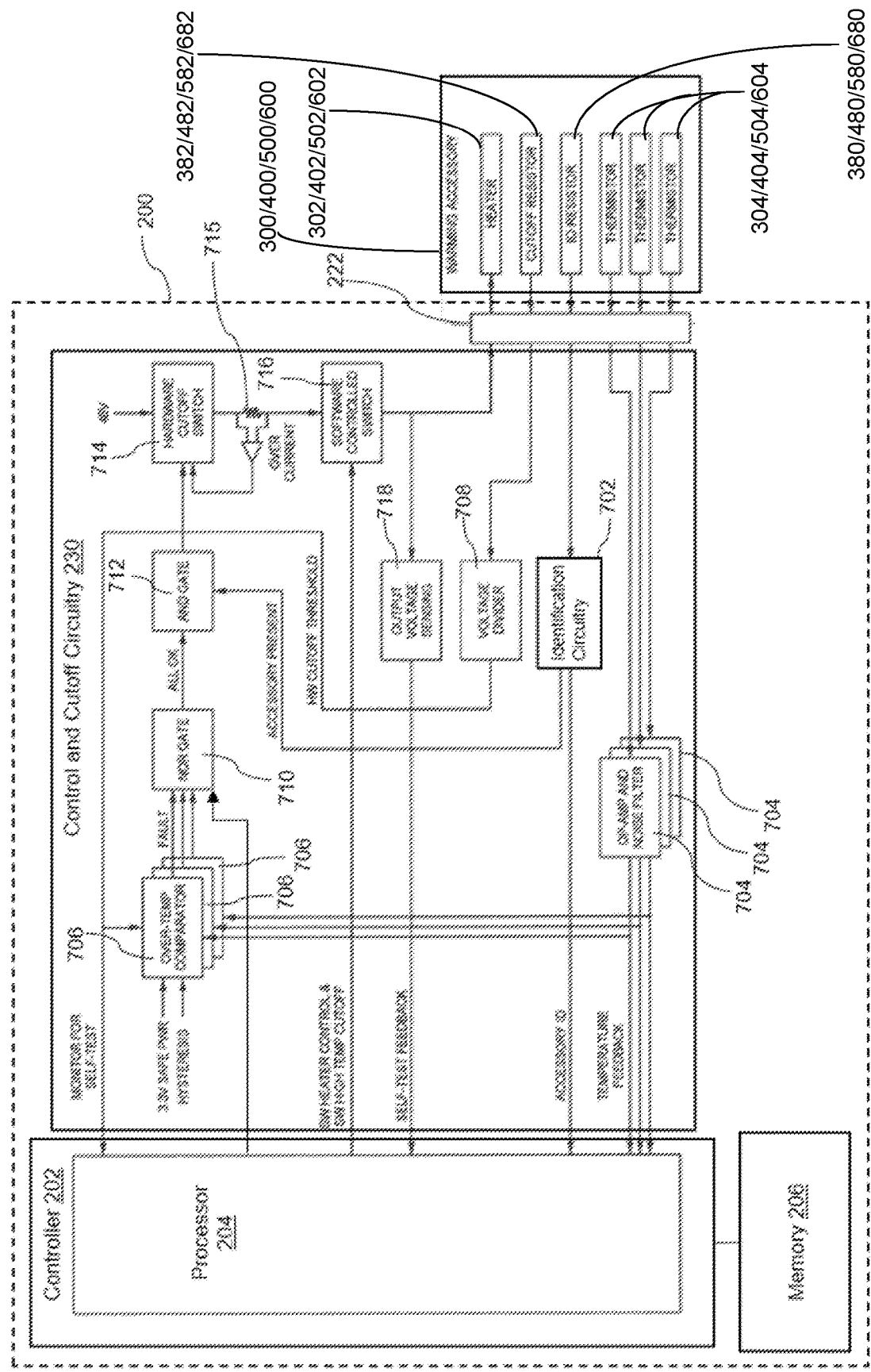
FIG. 12 is a schematic block diagram of parts of an exemplary control unit coupled to a warming device.

FIG. 12 shows an exemplary embodiment of control and cutoff circuitry 230. As shown, a warming device 300/400/500/600 is coupled to the control and cutoff circuitry 230 via the I/O interface 222. Operating power may be provided from the power interface 224 to the warming device 300/400/500/600 via the control and cutoff circuitry 230 and I/O interface 222. While the figures show one instance of control and cutoff circuitry 230 coupled to a respective warming device, will be appreciated that the control unit 200 may have multiple instances of control and cutoff circuitry 230, each which may be coupled to a respective warming device via the I/O interface. In some embodiments, each electrical connector (socket) of the I/O interface may be connected to a respective instance of a control and cutoff circuitry 230.

As described above, it may be possible to connect more than one type of warming device to a given electrical connector (socket) of the I/O interface. Identification of a connected warming device to the I/O interface 222 may be performed using warming device identification circuitry 702 when the warming device is plugged in. The identification circuitry 702 may be embodied as hardware. The warming device may include an identification resistor 380/480/580/680 therein, and the warming device identification circuitry 702 may be configured as a voltage divider including a resistor that may be used in combination with the identification resistor 380/480/580/680 of the warming device. The voltage value from the warming device identification circuitry 702 may be zero when no warming device is plugged in, and a unique non-zero value may be provided for each type of warming device when it is plugged into the I/O interface 222. This voltage value may be provided to the controller 202, and used together with the executed software (e.g., the application program 213 and/or the monitoring program 210) to determine when a warming device is plugged in, and to configure one or more parameters and/or settings, such as limits, tuning parameters, and GUI display appropriately for the connected warming device. As shown, the voltage value may also be used in the control and cutoff circuitry 230 as an indicator (e.g., as an input to gate 712) that a warming device is plugged in. The system may have multiple warming devices connected to the control unit, and different warming devices may have different user-interface and control requirements. Therefore, the controller 202 can determine which warming device or warming devices are connected and can vary the trip thresholds based on the type of warming device in use.

As described above, a warming device may include multiple temperature sensors. The control and cutoff circuitry 230 includes independent noise-filter and amplifier circuits 704 for each temperature sensor. The respective output signals from the independent noise-filter and amplifier circuits 704 each split and may be input to both the controller 202 and hardware over-temperature comparators 706. An analog-to-digital converter (not shown) may be used for purposes of inputting the output signals from the noise-filter and amplifier circuits 704 to the controller 202. The two branches of the temperature signal may be resistor isolated so that a misconfigured A/D converter input cannot affect the signal input to the hardware comparator. Independent over-temperature comparators 706 may be provided for each temperature sensor 304/404/504/604, and the output signal from a respective independent noise-filter and amplifier circuit 704 may be input to a respective independent over-temperature comparator 706. As described above, different warming devices may include different numbers of temperature sensors. The number of independent noise-filter and amplifier circuits 704 and the number of independent over-temperature comparators 706 may be such that they are each the same as or greater than the largest number of temperature sensors for a given warming device that may be used in the patient warming system. It will be appreciated that in the event a warming device is plugged in that has a fewer number of temperature sensors than the number of independent noise-filter and amplifier circuits 704 and the number of independent over-temperature comparators 706, some of the independent noise-filter and amplifier circuits and the number of independent over-temperature comparators may not be used in the control.

The threshold voltage for the overtemperature comparators 706 may be set by a resistive voltage divider 708. In some embodiments, an additional resistor 382/482/582/682 inside the warming device can modify the threshold set by the voltage divider 708. This may allow the threshold to accommodate the specific needs of that warming device.

Outputs from the overtemperature comparators 706 may be combined by logic gates such that any single over-temperature comparator can generate a fault and shut down the output for the corresponding warming device. As shown, the comparator outputs are input to NOR gate 710. The output from the NOR gate 710 may be input to AND gate 712. When the output from the NOR gate 710 indicates that no fault is present and is combined with a signal from the warming device identification circuitry indicating that the warming device is present, an output from the AND gate 712 may be output to the hardware cutoff switch 714 in order to close the switch and provide power. The hardware cutoff switch may be a first power switch in the control and cutoff circuitry 230 and is controlled by the hardware overtemperature comparators 706. When a warming device is plugged into the I/O interface, the hardware cutoff switch 714 is normally on (closed state) and turns off (open state) only in the event of an over-temperature cutoff (or during self-test). The hardware cutoff switch may in some embodiments include an over-current switch (e.g., a MOSFET) (not shown). The over-current switch may be configured as an electronic circuit breaker and may limit current during overloads, short circuits, and initial power-up (e.g., when internal capacitors are discharged and draw high charging currents) to protect the system from excessive current.

Current sensing circuitry 715 may be provided at the output of the hardware cutoff switch and may provide feedback to the hardware cutoff switch (e.g., to the over-current switch). In the event of over-current, the current sensing circuitry 715 may initially provide feedback to the hardware cutoff switch to limit the current, then after a short delay the feedback may cause the hardware cutoff switch to turn off the output. Overcurrent protection may help to prevent risks of excessive temperature, sparks, or fire in the event of a short circuit.

The controller 202 may execute the monitoring program 210 and may use temperature data (and in some embodiments, warming device identification inputs) from control and cutoff circuitry 230 to monitor temperature of the warming devices and control the supply of power to the warming devices in the event that an over-temperature situation and/or fault is detected.

The monitoring program 210 may be executed by the controller 202 to monitor temperature readings from the warming device and detect any temperature sensor in the connected warming device that is shorted or open.

The monitoring program 210 may be executed by the controller to drive a spare input of the NOR gate 710, such that it can generate (but not block) a fault. This allows for self-test of the gate and a shut-down mechanism.

The monitoring program 210 may be executed by the controller 202 to monitor (but not modify) the over-temperature threshold output by the voltage divider 708. This may help to ensure that the voltage divider 708 is working correctly and that any modification to the threshold is appropriate for the connected warming device (for that warming device's ID resistor).

The monitoring program 210 may be executed by the controller 202 to control a software-controlled switch 716. The software-controlled switch 716 is a second power switch included in the control and cutoff circuitry 230. The software-controlled switch may be used to pulse-width modulate the output power to the heating element for normal control. The software-controlled switch may also be used if the software detects an over-temperature condition. In other embodiments, the monitoring program 210 may be executed by the controller 202 to control a software-controlled switch (not shown) other than the software-controlled switch 716 used to pulse-width modulate the output power to the heating element for normal control.

An output voltage monitor 718 may monitor the voltage output to the warming device via the I/O interface 222, and outputs this information to the controller 202. The monitoring program 210 may be executed by the controller 202 to determine when power is applied to the heater. This may assist in detection of a failure of either power switch 714, 716.

The monitoring program 210 may be executed by the controller 202 to perform self-tests at power-on, when a warming device is plugged in, and/or during normal operation, to detect any hardware failures.

The control and cutoff circuitry 230 and the monitoring program 210 (as executed by the controller 202) may provide overtemperature protection by two redundant systems. The control and cutoff circuitry 230 provides an independent, hardware based system, that does not rely on the monitoring program 210. The redundancy of the control and cutoff circuitry and monitoring program (as executed by the controller) can detect and thereby protect against over-temperature even in the presence of a single failure.

The control and cutoff circuitry 230 and the monitoring program 210 (as executed by the controller 202) may also protect from undetected loss of redundancy. Redundant systems provide increased safety because the probability of both systems failing within a short period of time may be very low. However, the increased safety is lost if part of the system fails and the failure is undetected. In that case, a second failure, even years later, could cause a safety hazard.

The application program 213 via execution by the controller 202 may control the output of power to the heating element of the warming device. Control is conducted based on temperature input received from one or more of the temperature sensors of the warming device. The same temperature sensors of the warming device used in the over-temperature cutoff may be used in the power output control. In some embodiments, the temperature data received from the temperature sensors and output from the independent noise-filter and amplifier circuits 704 to the controller 202 may also be used in the output power control performed via the operating system. Because the temperature sensors of the warming device may be used for both overtemperature cutoff and power output control, duplication of the temperature sensors in the warming device is not needed. This allows for a reduction in cost associated with the warming device, as well as a reduction in the number of components present in the warming device (e.g., thermistors, wires, heat spreaders, etc.) that may cause X-ray artifacts.

In some embodiments, the warming device identification information provided to the controller 202 by the control and cutoff circuitry 230 may be used in setting parameters for power control. The control and cutoff circuitry 230 and the application program 213 (as executed by the controller 202) may allow for the monitoring and control of multiple warming devices connected to the control unit via respective connectors (e.g., sockets).

The application program 213 (as executed by the controller) may use the highest temperature reported by any temperature sensor in a heating zone to control the heating element of a warming device. Uncovered sensors generally report lower temperatures as compared to covered sensors, so the lower temperatures are disregarded to avoid excessive heating.

The application program 213 may be executed by the controller 202 to control operation of the software-controlled switch 716. Such control may be conducted in accordance with a set temperature (e.g., user-set or default) relative to the temperature detected by the temperature sensor(s).

The application program 213 may be executed by the controller 202 to cause the display to display a user interface to convey information about connected warming devices, warming device temperatures, alarms and other informational messages. An exemplary display is shown in FIG. 3.

The bootloader program 211 provides a facility to update the application program 213 and/or the monitoring program 210. The updated application program 213 and/or the updated monitoring program 210 may be provided through the service port 232 (e.g., USB). An exemplary operation of the bootloader program 211 in connection with the application program 213 is as follows: When the bootloader program starts, it will verify the cyclic redundancy check (CRC) of the bootloader program as part of a self-test. After a successful self-test, the bootloader program will check to see if there is a pending software update. If so, it will verify the integrity and authenticity of the update. If the check passes, it will copy the updated application from external flash into program flash and launch the application. If there is no pending software update, or the pending update fails its checks, the bootloader will verify the integrity and authenticity of the application currently residing in internal flash memory. If the application passes these checks, the bootloader will launch the application. If the current application check fails, the bootloader will look in external flash to see if there is an old version of the application stored there. If so, it will attempt to copy that to internal flash and run it. If no valid versions of the application can be found, the bootloader will halt and display an error code.

When not in standby, the responsibility of the application program 213 is to drive all the attached heating elements to the temperature selected by the user. It responds to user inputs from buttons to toggle the system between Standby and Active and to modify the temperature setpoint. The application program 213 may also be responsible for driving the LEDs and LCD that provide feedback to the user about the current system status.

Figure 13:
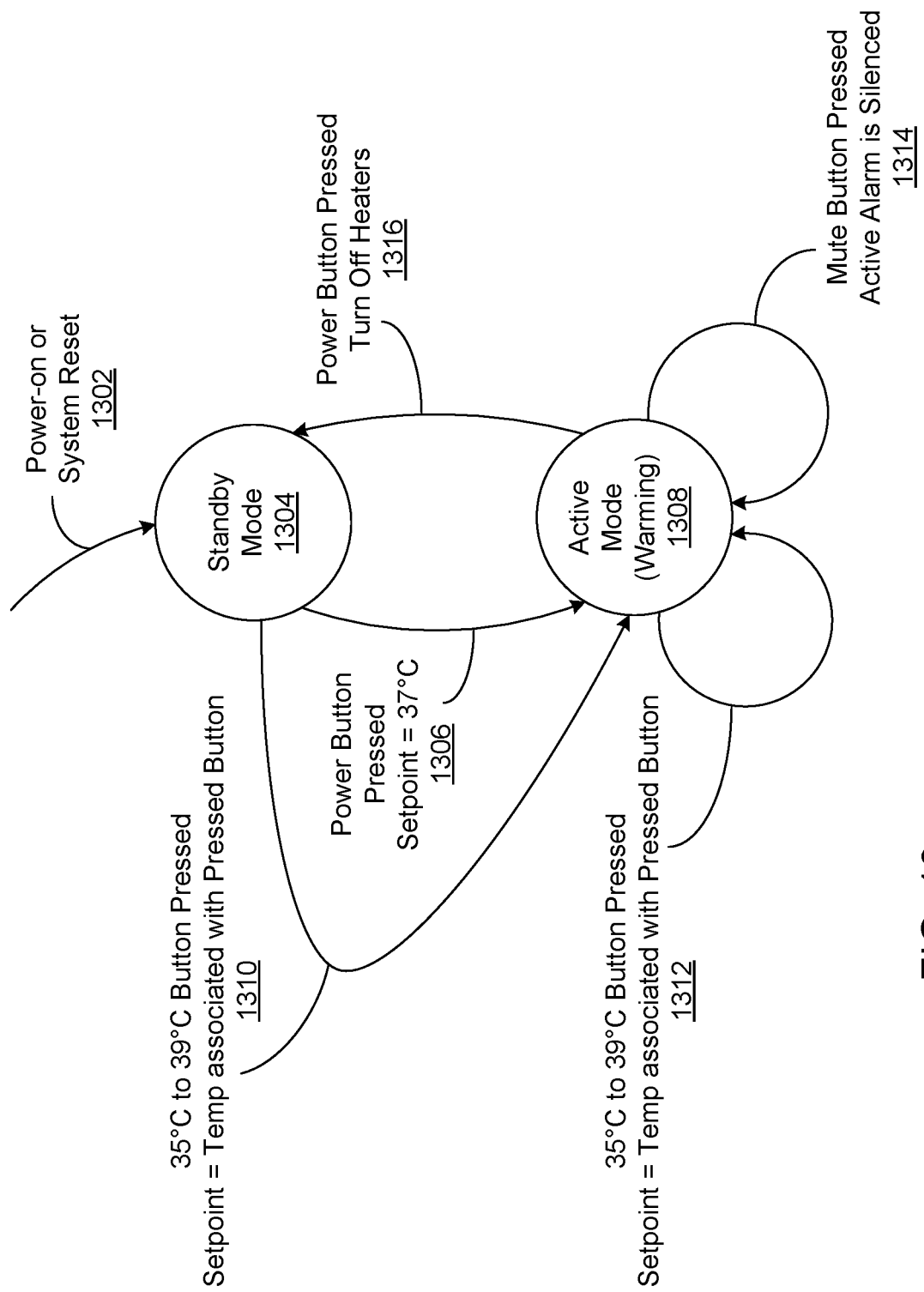
FIG. 13 is a flowchart showing an exemplary operation of the control system.

FIG. 13 provides a flowchart showing an exemplary operation of the application program 213 as executed by the controller. When the system is powered on (1302) and the application program 213 is executed, it enters standby mode (1304). If a user presses the Power/Standby button on the control unit (e.g., FIG. 3, button 266) (1306), the application program 213 is executed and switches to active mode (1308) with a default warming temperature setpoint. In some embodiments, the default warming temperature setpoint is 37° C. Alternatively, if the user presses a temperature setpoint button (e.g., FIG. 3, button 260, 261, 262, 263, 264) (1310), the application program 213 is executed and switches to active mode (1308) with the warming temperature set to the temperature selected by the user. When the system is in active mode, a user can change the temperature setpoint by selecting a different temperature (1312). If an alarm is activated (e.g., due to the detected temperature being above the set temperature, the alarm can be silenced using the mute button (1314). When the system is in active mode, if the user presses the power/standby button (1316) the system will return to standby mode (1304).

In some embodiments, the application program 213 is executed by the controller 202 to control all of the connected warming devices based on a single set temperature. In other embodiments, the application program 213 is executed by the controller 202 to control the connected warming devices separately based on independently selected set temperatures.

In some situations, a user may change a current set temperature of a warming device to a lower temperature. This may cause the new set temperature to be below the actual temperature of the warming device, particularly in cases where the warming device is already up to temperature. With reference to FIGS. 14A and 14B, in some embodiments, when a temperature setting (initial temperature setpoint 1402) of a warming device is adjusted (e.g., by the user) (temperature setpoint change 1408) to a temperature (new temperature setpoint 1410) lower than the current measured temperature (measured temperature 1406) of the warming device (step 1420), the application program 213 is executed by the controller 202 to monitor the rolling average of the temperature measurements (rolling average of temperature measurements 1412) (step 1422). The application program 213 will not issue an over-temperature alarm or warning if the rolling average of the temperature measurements decreases by at least a predetermined amount over a predetermined time period (step 1424). The application program 213 will issue an over-temperature alarm or warning if the rolling average decreases by less than a predetermined amount over a predetermined time period (steps 1424 and 1426). The predetermined amount over a predetermined time period may vary depending on the type of warming device. For example, in some embodiments, the predetermined amount over a predetermined time period for an over-body blanket is 1° C. per 10 seconds. As another example, in some embodiments, the predetermined amount over a predetermined time period for an underbody pad (which may include more heat retaining layers as compared to the over-body blanket) is 1° C. per minute. The temperature measurements (temperature sample measurements 1404) may be sampled at any suitable interval. In some embodiments, measurements are sampled every half second. In other embodiments, measurements are sampled every second. In other embodiments, measurements are sampled every five seconds.

Figure 15A:
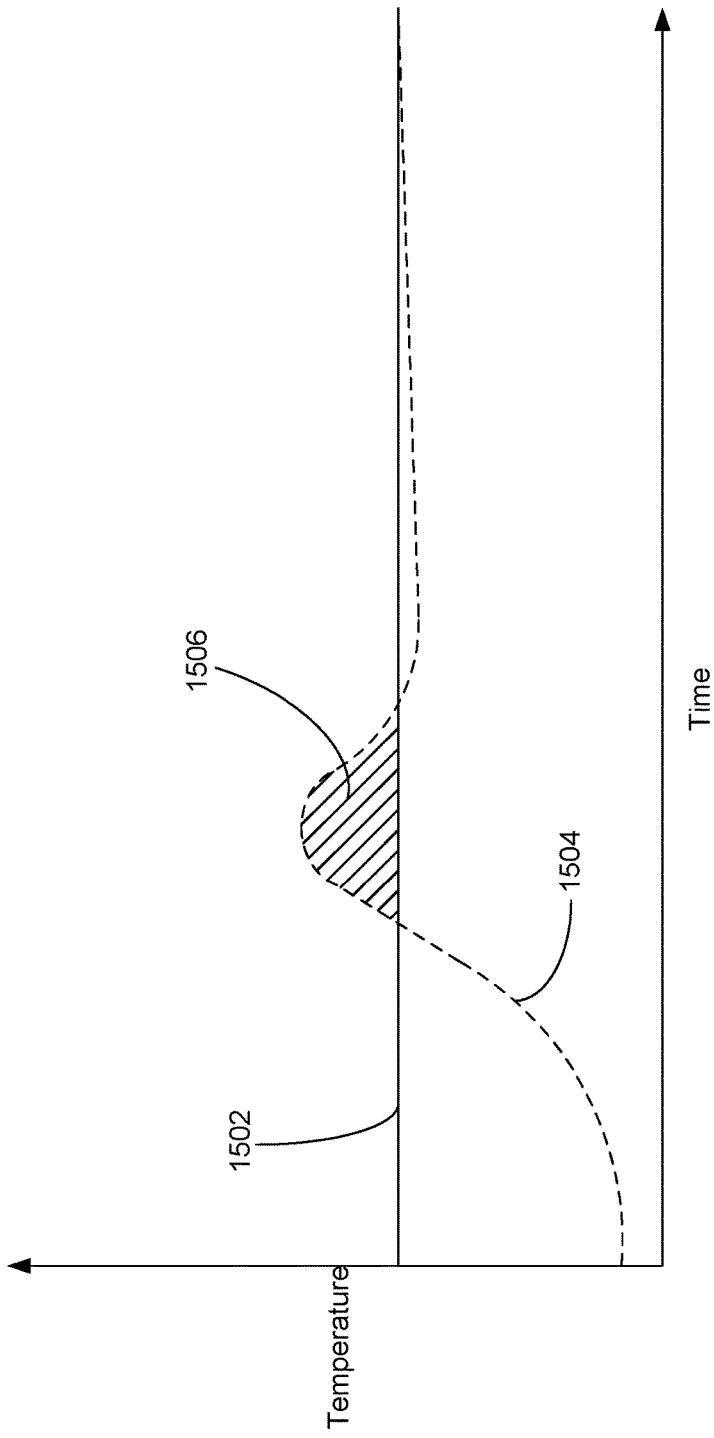
FIG. 15A is an exemplary temperature profile of a measured temperature over time relative to a temperature setpoint.
Figure 15B:
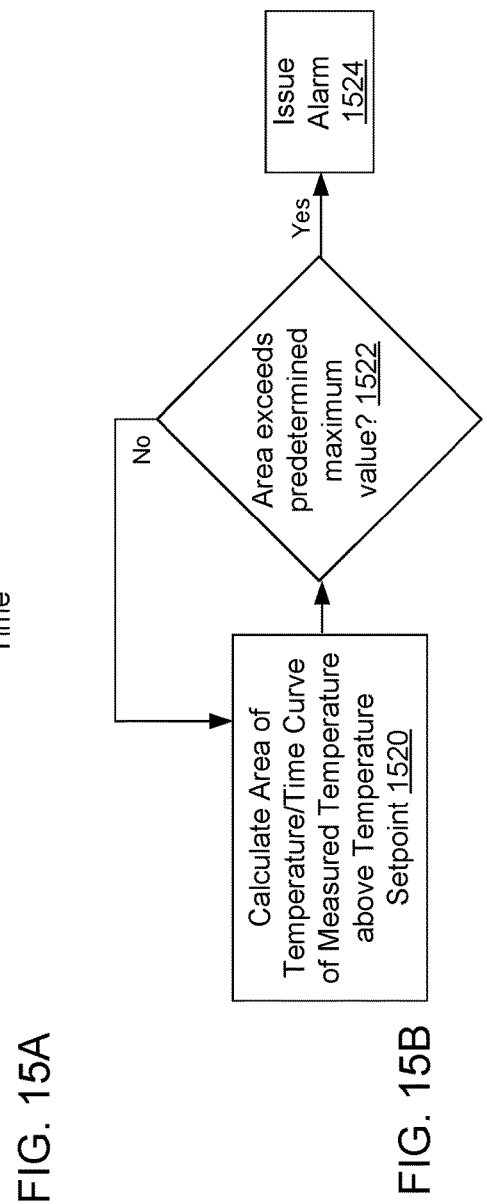
FIG. 15B is a flowchart in accordance with FIG. 15A.

In some situations, the measured temperature of the warming device may overshoot the set temperature. This may occur, for example, as a result of the warming device being heated to the set temperature upon startup, as a result of the user changing the current set temperature of the warming device to a higher temperature, and/or as a result of power being provided to the heating element while at a currently set temperature. With reference to FIGS. 15A and 15B, in some embodiments, if the temperature (measured temperature 1504) rises above the set temperature (temperature setpoint 1502), the application program 213 as executed by the controller 202 will not immediately issue an alarm. The application program 213 as executed by the controller 202 may issue an alarm based on the magnitude of the temperature above the set temperature as a function of time the temperature remains above the maximum allowable system temperature. As shown in FIG. 15A, the area of the temperature/time curve above the set temperature may be calculated (by the application program 213) (temperature differential multiplied by time 1506) (step 1520), and the over-temperature alarm will be issued only if the area exceeds a predetermined maximum value (steps 1522 and 1524). In some embodiments, the predetermined maximum value is in the range of 0.5° C. second to 2° C. second. In other embodiments, the predetermined maximum value is 1° C. second. The application program 213 as executed by the controller 202 may iteratively calculate the area when the measured temperature is above the set temperature. Because the amount of overshoot is a factor, the amount of time before an alarm issues will vary depending on how far the actual temperature is above the set temperature. This may help to avoid nuisance alarms. In some embodiments, the application program will also trigger an alarm after a maximum amount of time over the set temperature. In some embodiments, the maximum amount of time is 4 seconds. In other embodiments, the maximum amount of time is 3 seconds. The application program 213 as executed by the controller 202 may reset the calculated area to zero upon the measured temperature lowering to the set temperature.

As described above, application program 213 may be executed by the controller 202 to control the output of power to the heating element of a warming device based on a highest temperature sensor reading. These temperature sensors may be part of a zone associated with a given heating element. However, some warming devices may include more than one heating element. As such, these different heating elements may be controlled as separate zones of a warming device, with respective groups of temperature sensors associated with the different zones. For example, FIG. 1 schematically shows an underbody pad 300 having two different heating elements 302, each heating element having sensors 304 associated therewith. In some embodiments, the multiple heating elements of the warming device may be controlled independently of one another (separate and independent control of each zone based on the highest temperature sensor reading from that zone). In other embodiments, the multiple heating elements of the warming device may be controlled dependently of one another (control the heating elements of both zones based on the highest overall temperature sensor reading among the zones). In accordance with this dependent control, both heating elements are controlled in the same manner (e.g., same amount of power) based on the highest temperature reading.

In other embodiments, the multiple heating elements of the warming device may be controlled in a floating manner in which the power supplied to the heating element(s) of one zone is controlled to be within a predetermined amount of the power supplied to the heating element(s) of another zone. In accordance with the floating control, control of the heating elements of both zones is at least in part based on the highest overall temperature sensor reading among the zones, but the amount of power applied to the heating element(s) of a zone having a highest zone temperature that is less than the highest overall temperature is limited to an amount over the amount of power applied to the heating element(s) of the zone having the highest overall temperature (relative to its maximum power).

As an example, the percentage of power (relative to its maximum power) applied to the heating element(s) of a zone having a highest zone temperature that is less than the highest overall temperature may at most be set to a value that is within a predetermined percentage higher than the percentage of power (relative to its maximum power) applied to the heating element(s) of the zone having the highest overall temperature. For example, in a floating control situation where a two-zone, two heating element warming device is controlled using a 37° C. set point with a predetermined floating control percentage of 5%, and the highest temperature in zone 1 is 37° C. whereas the highest temperature in zone 2 is 36° C., the heating element of zone 1 may be operated at 0% power, and the heating element of zone 2 is limited to operation at no more than the predetermined percentage above zone 1 (e.g., 5%). In some embodiments, the predetermined percentage is up to 75% higher than the percentage of power (relative to its maximum power) applied to the heating element(s) of the zone having the highest overall temperature. In other embodiments, the predetermined percentage is up to 50% higher than the percentage of power (relative to its maximum power) applied to the heating element(s) of the zone having the highest overall temperature. In other embodiments, the predetermined percentage is up to 25% higher than the percentage of power (relative to its maximum power) applied to the heating element(s) of the zone having the highest overall temperature. In other embodiments, the predetermined percentage is up to 10% higher than the percentage of power (relative to its maximum power) applied to the heating element(s) of the zone having the highest overall temperature. In other embodiments, the predetermined percentage is up to 5% higher than the percentage of power (relative to its maximum power) applied to the heating element(s) of the zone having the highest overall temperature.

The floating control may be particularly advantageous in a situation where at least one of the temperature sensors in one heating zone is covered, but the temperature sensors in the adjacent heating zone are not. By supplying power to the first zone within a predetermined amount of the power supplied to the second zone, this may allow for flexibility to heat different zones (which may have different heating requirements for a given patient), while also preventing different heating zones from heating to substantially different temperatures.

Figure 16:
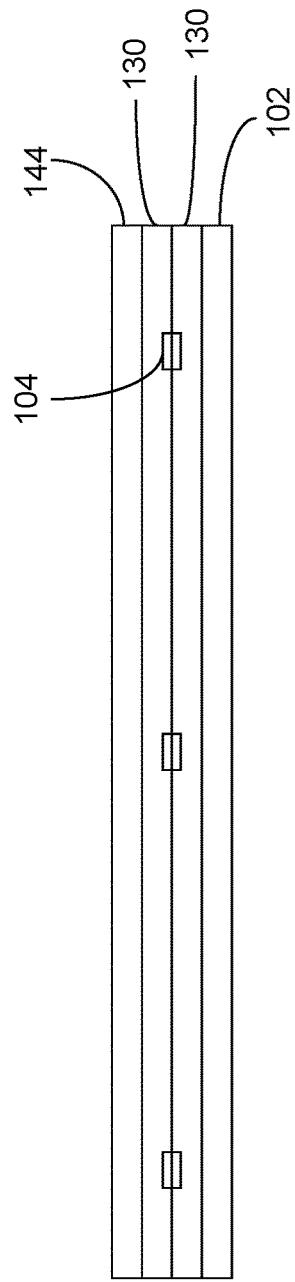
FIG. 16 is a schematic side view of parts of an exemplary warming device.
Figure 17:
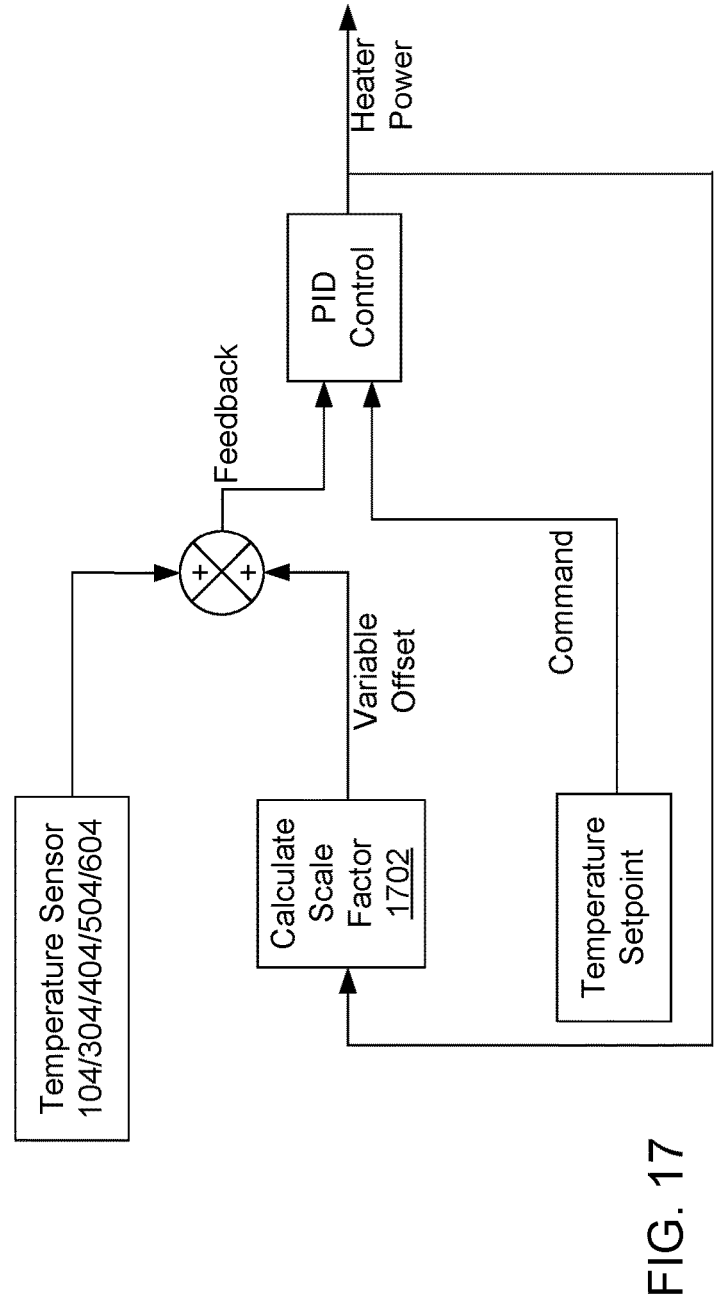
FIG. 17 is a schematic representation of exemplary power control based in part on temperature data provided by temperature sensor(s) spaced from the contact surface of an exemplary warming device.

As described above, application program 213 may be executed by the controller 202 to control the output of power to the heating element based on the highest temperature sensor reading received from the temperature sensors. For some warming devices, the temperature sensors are adjacent the outer layer of the warming device. For example, FIGS. 10 and 11 show the layers of an exemplary warming blanket 400 in which the temperature sensors 404 are adjacent an inner surface of the cover 438 of the blanket. In this embodiment, the close proximity of the temperature sensors 404 to outer surface of the cover (the contact surface of the warming device) may provide an accurate reading of the temperature of the contact surface of the warming device. For other warming devices, the temperature sensors are spaced apart from the outer layer of the warming device. For example, FIGS. 8 and 9 show an exemplary underbody pad 300 in which the temperature sensors 304 are spaced from the cover 344 of the underbody pad by a spacer layer 330. Similar spacing is also exemplified by the schematic layer structure of an exemplary warming device shown in FIG. 16. The temperature sensors 104 may be spaced from the heating element 102 by one or more spacer layers 130. A spacer layer 130 and/or one or more other suitable layers may be disposed between the temperature sensors 104 and the cover layer 144 for reasons such as pressure management. However, spacing between the temperature sensors 104 and the cover layer 144 can cause an unacceptable difference between the measured temperature and the actual temperature at the contact surface of the warming device. In some embodiments, this spacing may range from 4 millimeters to 20 millimeters. In other embodiments, this spacing may range from 4 millimeters to 10 millimeters. Accordingly, in some embodiments, the application program 213 (as executed by the controller 202) will compensate for temperature readings of these "proxy" temperature sensors. This offset between the proxy temperature and the target temperature can be constant or can be variable to account for environmental or thermal load changes. FIG. 17 schematically shows exemplary introduction of a scale factor (calculate scale factor 1702) to adjust the temperature sensor (104/304/404/504/604) measured temperature. The thermal characterization of the warming device and of the proxy temperature are known and a correlation is used to determine between the two to use as the controlling schema for the system. The control shown in FIG. 17 may be performed by the application program 213 as executed by the controller 202.

In some embodiments, for warming devices that use proxy temperature sensors, a variable temperature offset may be used to compensate for when a loading situation changes, such as when a patient lay on an underbody warming device (e.g., a loaded state). Different thermal characterizations of the warming device may be used for the loaded state and the unloaded state. This adjustment can vary one or more parameters such as heater power or heater current and can adjust the assumed patient contact surface temperature as needed. In an example, the loading situation may be detected by one or more pressure sensors (not shown) in the warming device.

The control unit 200 may have a maximum power budget that it can collectively deliver to the connected warming devices at any given time. In some embodiments, when the connected warming devices are at room temperature and/or are heating to the set temperature, the application program 213 may be executed by the controller 202 to provide power to warming device heating zones in a budgeted manner that avoids exceeding the total power budget for the system. This is because the power requirement of a given warming device at a point in time may be such that it requires the majority (or all) of the available power, and power would therefore not be able to be shared among two or more connected warming devices at the same time. The budgeted allocation may be predetermined and defined by the application program 213. For example, in a situation where an underbody pad 300, over-body blanket 400, and headrest 500 are connected to the control unit 200, at start up with the warming devices at room temperature, 50% of the power "on-time" might be provided to the underbody pad with the remainder spread across the over-body blanket and headrest. Also, the 50% of the dedicated "on-time" for the underbody pad may be divided so that the heating element(s) of only one of the two heating zones of the underbody pad is on at a time. By controlling the budget in this way, and depending on the consumption of the heating element(s) of each warming zone, the system may turn on all the different zones at different phases with no overlap.

This approach of sharing of available current amperage from the power supply across the warming devices sets the raise edge of a pulse to one heating element at the beginning of a phase, sets the fall edge of a pulse to another heating element at the end of a phase (e.g., the same phase or different phase), and sets the location of a fall edge of the pulse to the one heating element and the raise edge of the pulse to the another heating element so they are adjacent one another but do not overlap. The location of the fall edge of the pulse to the one heating element and the raise edge of the pulse to the another heating element may be adjusted depending on the heating needs and/or the priority of the warming devices. This approach may allow for the on time of the power to accommodate 100% utilization if needed.

FIGS. 18A-18C show an exemplary embodiment of the power budgeting between multiple warming devices as performed by the application program 213 executed by the controller 213. In some embodiments, Acc1 may correspond to the heating element of a headrest, Acc2 may correspond to the heating element of an over-body blanket, and Acc3, Zone 1 and Acc3, Zone 2 may correspond to the heating elements of an underbody pad. There are four heating elements, and the on/off control thereof is a quarter of the PWM duty cycle. As shown in FIG. 18A, the on-time for half of the heating elements (Acc1 and Acc3, Zone 1) is set by setting the raise edge at the beginning of a respective phase segment (0° and 180°, respectively) (step 1802), and the off-time of the other half of the heating elements (Acc 2 and Acc3, Zone 2) is set by setting the fall edge of pulse at the end of a respective phase segment (180° and 0°, respectively) (step 1804). The location of the fall edge of the pulse to Acc1 and the raise edge of the pulse to Acc2 are each respectively set between 0° and 180° such that they are adjacent one another but do not overlap (step 1806). Similarly, the location of the fall edge of the pulse to Acc3, Zone1 and the raise edge of the pulse to Acc3, Zone 2 are each respectively set between 180° and 0° such that they are adjacent one another but do not overlap. Subsequent to this initial set, the adjacent raise edge and fall edge may be adjusted (step 1808). Arrows represent the increasing "on" time of the heating zone. In some embodiments, this adjustment may allow up to 100% of the available phase to be utilized. This is exemplified in FIG. 18B, which represents an exemplary adjustment by the application program 213 as executed by the controller 202 to the initial setting of FIG. 18A. At initial startup there may be less than 100% utilization, however using this heuristic the system may learn about the warming device heating needs and the on time may grow to accommodate 100% utilization if needed.

As the warming devices heat, the power requirement of the heating element(s) of each warming device may decrease due to the PTC heater technology used in the heating zones, and "on-time" overlap between two or more warming devices may be possible. As heating continues and the power requirement becomes less, it is possible that all warming devices may be on at the same time overlap. Therefore, the heating element(s) of each warming device can have a PWM duty cycle of up to 100% if needed.

Figure 19:
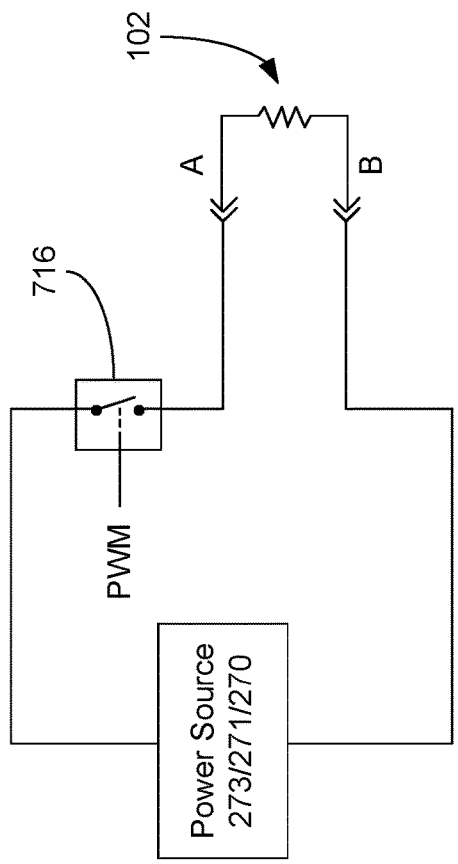
FIG. 19 is a schematic diagram of exemplary circuitry for applying pulse width modulation to a resistive heater.
Figure 21:
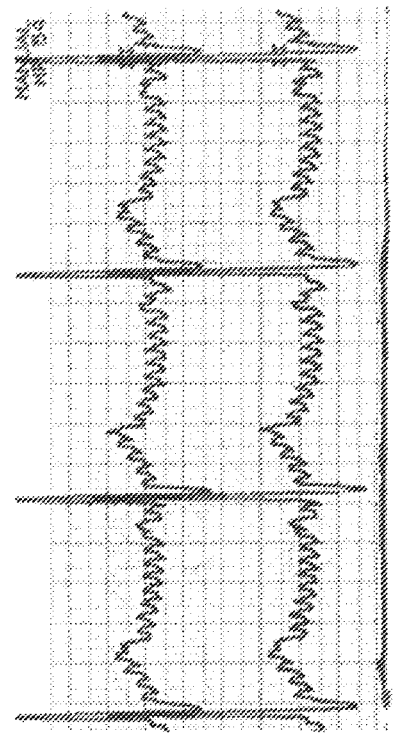
FIG. 21 is an exemplary electrocardiogram.
Figure 20:
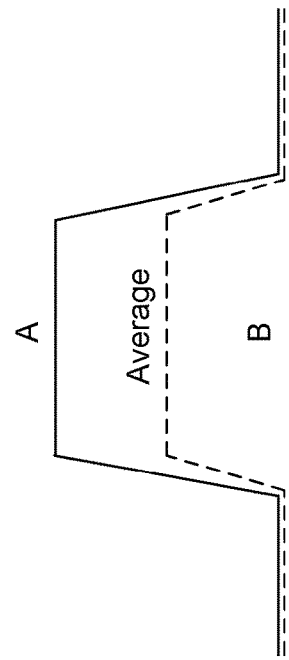
FIG. 20 is a graphical representation of the biased voltage of the resistive heater of FIG. 19.

As described above, the software-controlled switch may be used to pulse-width modulate the output power to the heating element for normal control. FIGS. 19-21 show an example in which the software-controlled switch 716 is coupled to one end of the heating element 102 between the heating element and the positive terminal of the power source 273/271/270 (e.g., via the power interface 224), while the other end of the heating element is connected to the negative terminal of the power source 273/271/270. It will be understood that a variation of the example shown in FIG. 19 has the software-controlled switch placed in the negative lead instead of the positive lead. The heating element is a conductive object near the patient, and forms one plate of a capacitor, the patient's body being the other plate. Any change in voltage on the heating element is capacitively coupled to the patient. The resulting voltage on the patient is very small and does not represent a shock hazard, but it could interfere with ECG monitors which measure voltages in the range of millivolts. As shown in FIG. 20, when the switch 716 is on, the heating element is biased to a voltage (Average) midway between the positive and negative power terminals (A and B), and when the switch is off the heating element is at the negative supply voltage. This represents a voltage difference between the switch-on and switch-off states which can be coupled to the patient. As shown in FIG. 21, this may result in unwanted interference with ECG monitors or other sensitive electronics in the operating room.

Figure 22:
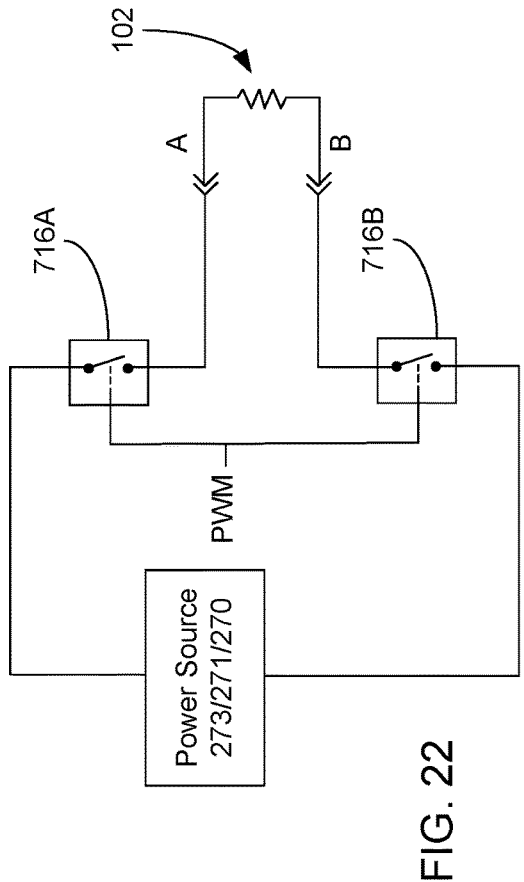
FIG. 22 is a schematic diagram of exemplary circuitry for applying pulse width modulation to a resistive heater.
Figure 23:
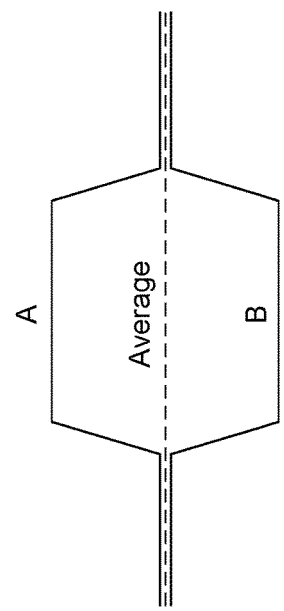
FIG. 23 is a graphical representation of the biased voltage of the resistive heater of FIG. 22.
Figure 24:
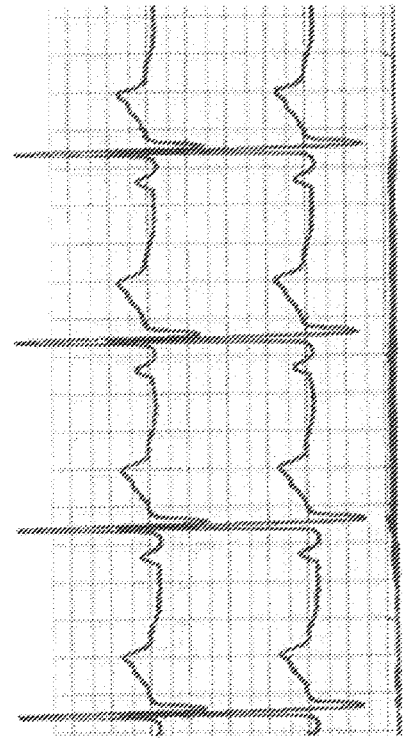
FIG. 24 is an exemplary electrocardiogram.

With additional reference to FIGS. 22-24, in some embodiments, the control unit may utilize a differential drive. The differential drive makes it possible to use a DC PWM minimizing or eliminating interference on other operating room equipment such as ECG monitors or other sensitive electronics. As contrasted with that shown in FIG. 19, the software-controlled switch 716 is embodied as a plurality of switches 716A, 716B provided at both ends, one to the positive terminal of the power source 273/271/270 (e.g., via the power interface 224) and one to the negative terminal of the power source 273/271/270 (e.g., via the power interface 224). As shown in FIG. 23, when the switches are off, the heating element is biased to a voltage (Average) midway between the power source terminals (A and B). This is the same voltage as when the switches are on. Due to the balanced nature of the drive, the charge coupled to the patient from one end of the heating element tends to cancel out the charge coupled from the other end, greatly reducing the voltage coupled to the patient. The voltage coupled to the patient is an attenuated version of the average heater voltage. As shown in FIG. 24, this may result in reduction or elimination of the interference with ECG monitors or other sensitive electronics in the operating room, as is present in FIG. 21.

The above observations are valid regardless of whether the positive terminal, the negative terminal, or neither terminal of the power source is grounded.

In some embodiments, the application program may be executed by the controller to operate the software-controlled switch 716 (using PWM) at a predetermined frequency. The heater PWM may be at any suitable frequency. In some embodiments, the PWM frequency may be set to match that of the AC power line (e.g., 60 Hz). This frequency selection may be manually set/modified, or automatic set/modified per detection of the AC supply by the system. ECG monitors and other sensitive operating room equipment are often designed to reject electrical noise coming from the AC power line. Therefore, setting the PWM frequency to match the line frequency may reduce or eliminate interference with such equipment.

As described above, and with continued reference to FIG. 3, the control unit includes a housing 250. With additional reference to FIGS. 25 and 26, a support apparatus 900 may be attached to (or form a part of) the housing 250. The support apparatus may be configured to attach the housing to either of a vertical shaft (e.g., a support structure such as an IV pole) or a horizontal shaft (e.g., a support structure, bed rail, and the like). It will be understood that the support apparatus can be secured to other suitable support structures having a vertical and/or horizontal structure for attachment.

The support apparatus 900 includes a lateral acting clamp 902 for securing the support apparatus 900 to a vertical support. The vertical support structure may in some embodiments have a round, rectilinear, or polygonal cross-sectional shape. In the embodiment shown, the lateral acting clamp 902 is a generally C-shaped clamp member including a back portion 904, a first arm 906, and a second arm 908, which together define a channel 910. A threaded post 912 includes a knob 914 attached to a proximal end thereof and a block 916 at the distal end thereof. The first arm 906 includes a threaded hole 918 formed through it, generally across from the second arm 908, into which the threaded post 912 screws. Thus, the support apparatus 900 may be secured to a vertical support structure by unscrewing the threaded post 912 sufficiently to open up space in the channel 910, positioning the later acting clamp 902 around the vertical support structure, and screwing the threaded post 912 down against the side of the IV pole, whereby the IV pole is clamped between the block 916 and the second arm 908.

In other embodiments (not shown), the threaded post 912 and knob 914 may instead be embodied as a different lateral member, such as a cam lock.

Figure 28:
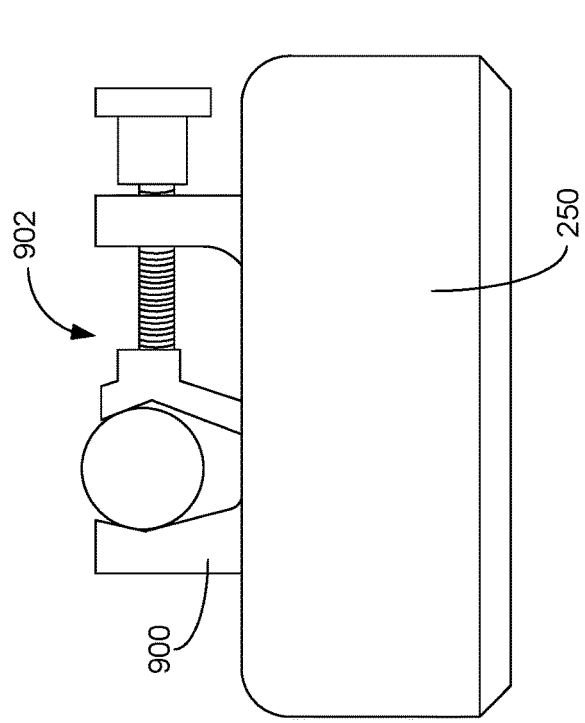
FIG. 28 is a schematic top view showing an exemplary control unit and support apparatus mounted vertically to a pole.
Figure 27:
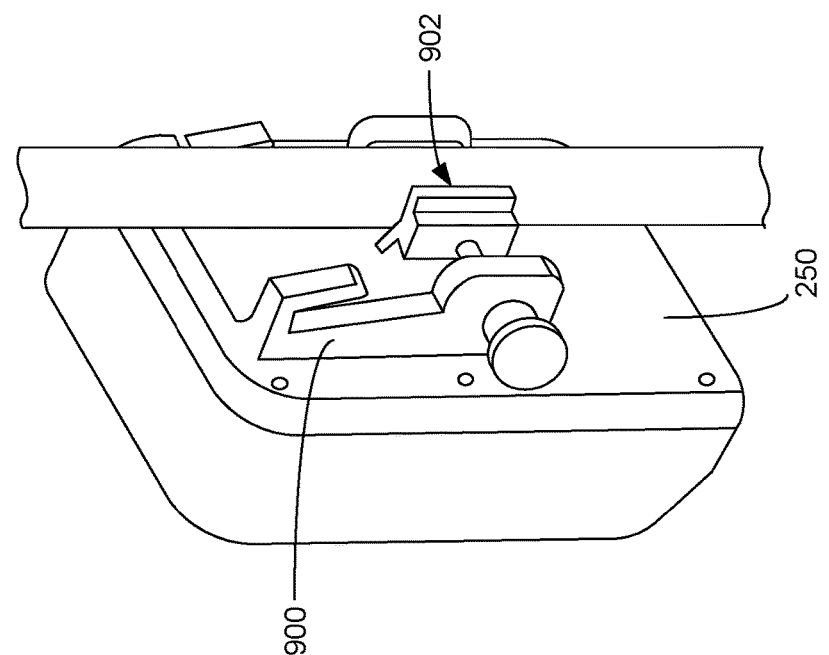
FIG. 27 is a schematic perspective view showing an exemplary control unit and support apparatus mounted vertically to a pole.
Figure 30A:
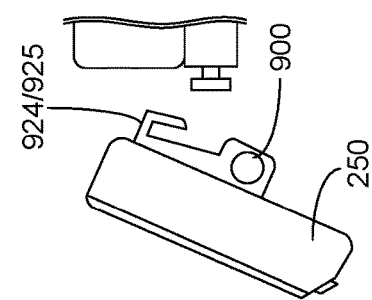
FIGS. 30A-30D are schematic side views showing horizontal mounting of an exemplary control unit and support apparatus.
Figure 30B:
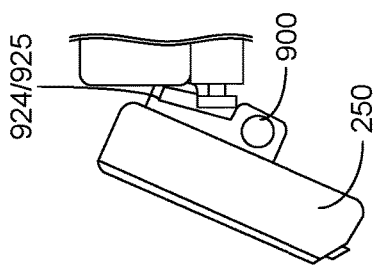
Figure 30C:
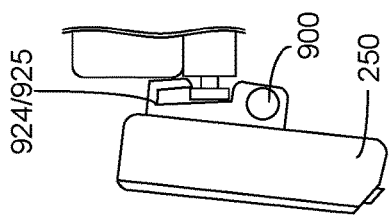
Figure 30D:
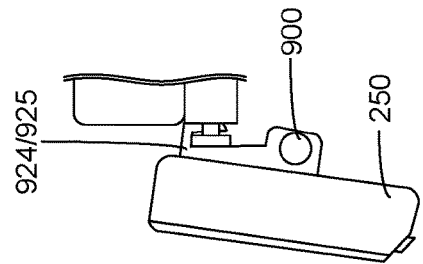
Figure 31A:
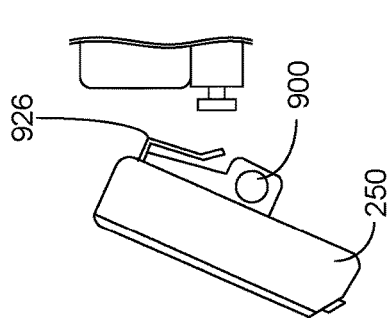
FIGS. 31A-31D are schematic side views showing horizontal mounting of an exemplary control unit and support apparatus.
Figure 31B:
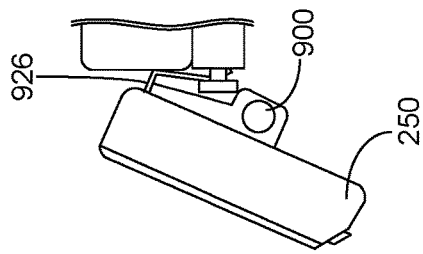
Figure 31C:
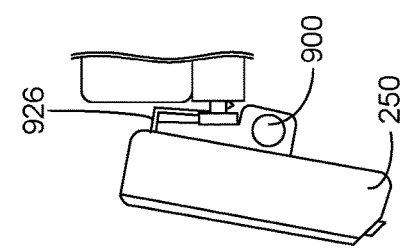
Figure 31D:
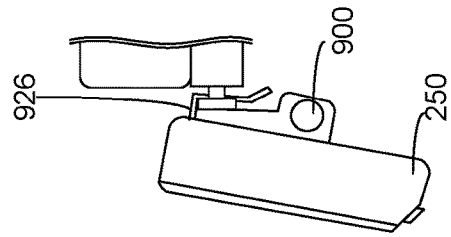

In the embodiment shown, the block 916 of the threaded post and the second arm include a planar contact surface 920. In other embodiments, the block of the threaded post and/or the second arm may be shaped to assist with clamping to the vertical support structure. With additional reference to FIGS. 27 and 28, the block 916 is shaped as a V block and the second arm 908 has a V-shaped indentation for the contact surface 920. FIGS. 27 and 28 show an exemplary installation of the support apparatus on a vertical pole.

Figure 25:
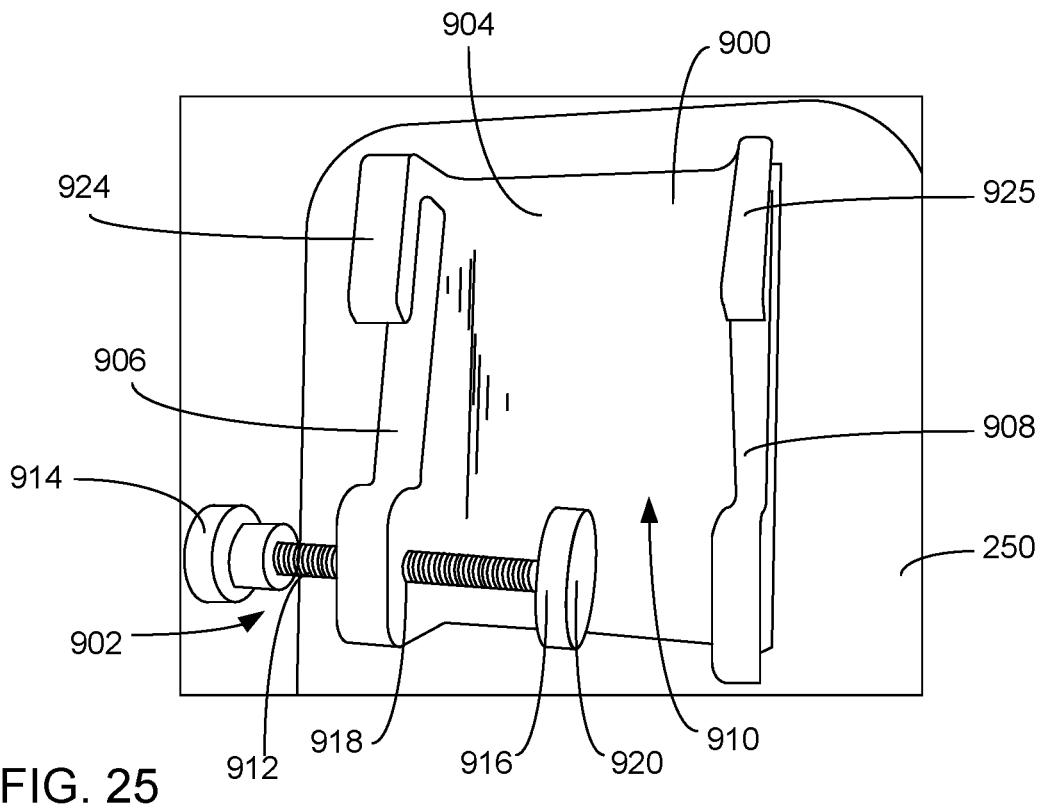
FIG. 25 is a schematic rear perspective view of an exemplary control unit including a support apparatus.
Figure 26:
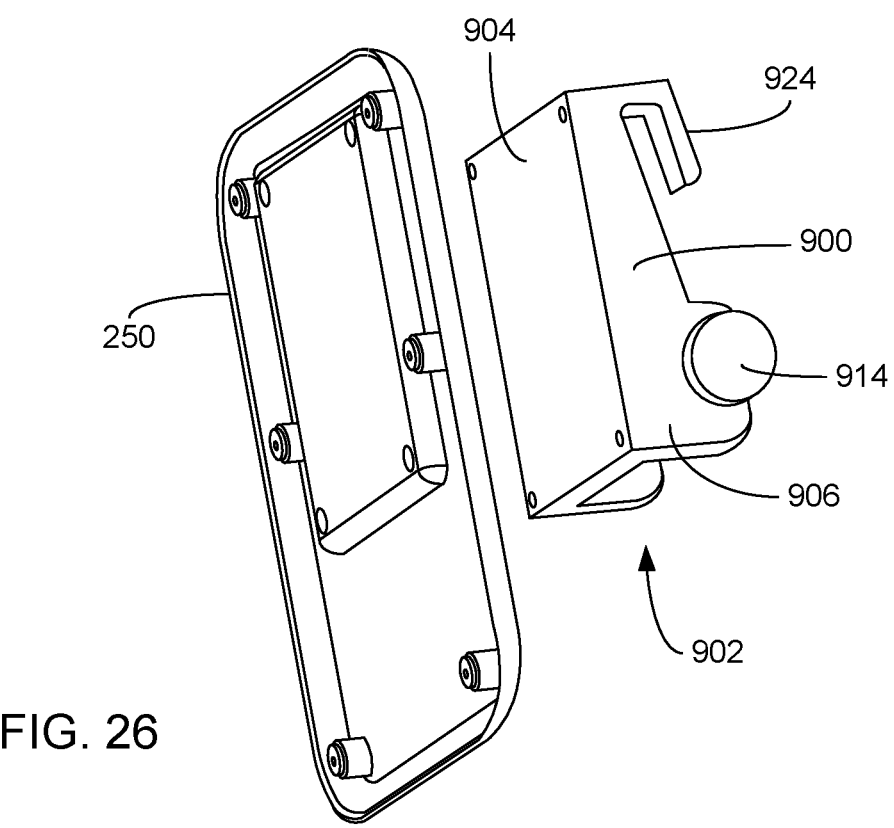
FIG. 26 is an exploded schematic view of parts of an exemplary control unit and support apparatus.
Figure 29:
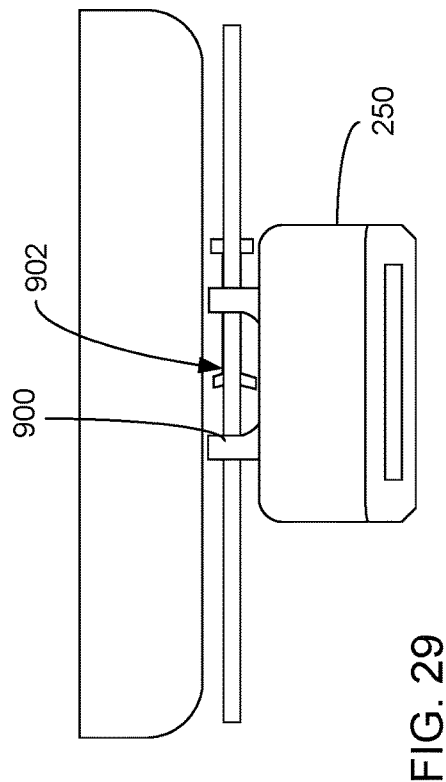
FIG. 29 is a schematic top view showing an exemplary control unit mounted horizontally to a bed rail.

With continued reference to FIGS. 25 and 26, a portion of the first arm 906 is shaped as a hook 924 extending from the back portion 904, and a portion of the second arm 908 is shaped as a hook 925 extending from the back portion 904. In some embodiments, the hooks 924,925 are rigid, provide a semi labyrinth opening, and are configured to be hung on a horizontal rectilinear rail. FIG. 29 shows an overhead view of the support apparatus 900 mounted to a horizontal bed rail. FIGS. 30A-30D show an exemplary installation of the support apparatus 900 on a rectilinear rail.

FIGS. 31A-31D show another exemplary embodiment of hooks provided as part of the support apparatus 900. In this embodiment, one or more sprung rail hooks 926 are used in place of the rigid hooks. The sprung rail hooks 926 may be separate elements from the first arm 906 and second arm 908, and may be secured to the back portion 904. FIGS. 31A-31D show an exemplary installation of the support apparatus including the sprung rail hooks 926 on a rectilinear rail. An advantage to this approach is the ability to adapt to different rail form factors (e.g., round, rectilinear, or polygonal cross-sectional shape).

With reference to FIG. 26, in some embodiments, the support apparatus 900 may be secured to the housing 250 via one or more fasteners (e.g., screws, adhesive, etc.). The fasteners may in some embodiments be secured through the housing such that they are not visible when the housing and support apparatus are assembled. When secured to the housing 250, the support apparatus may be rigidly maintained at the back of the housing 250.

Figure 32:
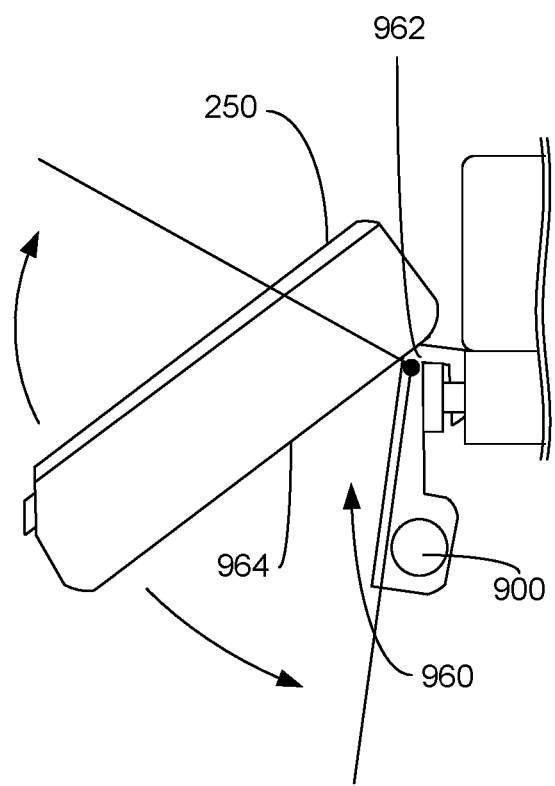
FIG. 32 is a schematic side view showing an exemplary control unit and support apparatus.

FIG. 32 shows another exemplary embodiment of the support apparatus, in which a hinge assembly 960 is included with the support apparatus 900. The hinge assembly 960 may include a hinge 962 and an interface bracket 964. The interface bracket 964 may be secured to the housing in place of the back portion. This allows the housing 250 to move/pivot with respect to the support apparatus 900. As such, an end user can angle the device for better viewing or interaction. A detent, friction, or locking feature (not shown) can be added to hold the control unit at a desired angle.

Although the invention has been shown and described with respect to certain preferred embodiments, it is understood that equivalents and modifications will occur to others skilled in the art upon the reading and understanding of the specification and the attached drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application. The present invention includes all such equivalents and modifications and is limited only by the scope of the following claims.

What is claimed is:

1. A patient warming system, comprising:
a control unit comprising:
an I/O interface comprising two or more connectors, the two or more connectors having a same configuration;
a controller configured to execute a program stored in a memory of the control unit that identifies a warming device plugged into one of the two or more connectors and that controls application of power to the warming device relative to a set temperature and in accordance with the identity of the warming device;
warming devices interchangeably coupled to the control unit via the I/O interface, each warming device comprising:
one or more heating elements;
one or more temperature sensors; and
a connector that is configured to be coupled to any one of the two or more connectors,
wherein the program as executed by the controller:
monitors a rolling average of temperature measurements from the one or more temperature sensors when the set temperature is changed to a temperature lower than a current measured temperature; and
issues an over-temperature alarm or warning if the rolling average decreases by less than a predetermined amount over a predetermined time period.

2. The patient warming system of claim 1, wherein the one or more heating elements are positive temperature coefficient heating elements.

3. The patient warming system of claim 1, wherein the program as executed by the controller budgets application of power among two heating elements via pulse width modulation by:
setting a raise edge of a pulse to one of the heating elements at a beginning of a phase;
setting a fall edge of a pulse to another heating element at an end of another phase; and
setting a location of a fall edge of the pulse to the one heating element and the raise edge of the pulse to the another heating element so they are adjacent one another but do not overlap.

4. The patient warming system of claim 3, wherein the program as executed by the controller adjusts one or both of the location of the fall edge of the pulse to the one heating element and the raise edge of the pulse to the another heating element.

5. The patient warming system of claim 4, where the program is configured to adjust the location of the fall edge of the pulse to the one heating element and the raise edge of the pulse to the another heating element such that the gap is eliminated.

6. The patient warming system of claim 3, wherein, as set, there is a gap between the location of the fall edge of the pulse to the one heating element and the raise edge of the pulse to the another heating element.

7. The patient warming system of claim 1, wherein each warming device comprises an identification resistor; and the control unit comprises warming device identification circuitry, the warming device identification circuitry configured as a voltage divider including a resistor that is configured to be used in combination with an identification resistor of a warming device to output a non-zero value.

8. The patient warming system of claim 1, wherein the predetermined amount over a predetermined time period is 1° C. per 10 seconds.

9. The patient warming system of claim 1, wherein the predetermined amount over a predetermined time period is 1° C. per 1 minute.

10. A patient warming system, comprising:
a control unit comprising:
an I/O interface comprising two or more connectors, the two or more connectors having a same configuration;
a controller configured to execute a program stored in a memory of the control unit that identifies a warming device plugged into one of the connectors and that controls application of power to the warming device relative to a set temperature and in accordance with the identity of the warming device;
warming devices interchangeably coupled to the control unit via the I/O interface, each warming device comprising:
one or more heating elements;
one or more temperature sensors; and
a connector that is configured to be coupled to any one of the two or more connectors,
wherein the program as executed by the controller:

calculates an area of a temperature curve of a temperature measured by the one or more temperature sensors over the set temperature as a function of time when the measured temperature is above the set temperature; and issues an over-temperature alarm or warning if the calculated area exceeds a predetermined maximum value.

11. The patient warming system of claim 6, wherein the predetermined maximum value is in the range of 0.5° C. second to 2° C. second.

12. A The patient warming system, comprising:
a control unit comprising:
an I/O interface comprising two or more connectors, the two or more connectors having a same configuration;
a controller configured to execute a program stored in a memory of the control unit that identifies a warming device plugged into one of the connectors and that controls application of power to the warming device relative to a set temperature and in accordance with the identity of the warming device;
warming devices interchangeably coupled to the control unit via the I/O interface, each warming device comprising:
one or more heating elements;
one or more temperature sensors; and
a connector that is configured to be coupled to any one of the two or more connectors,
wherein one of the warming devices comprises two heating elements and at least two temperature sensors, each of the heating elements having at least one of the temperature sensors associated therewith, and the program as executed by the controller to control the two heating elements at least in part based on a highest overall temperature sensor reading of the warming device, wherein a percentage of power relative to its maximum power applied to the heating elements of a zone having a highest zone temperature that is less than the highest overall temperature is at most set to a value that is within a predetermined percentage higher than the percentage of power relative to its maximum power applied to the heating elements of the zone having the highest overall temperature.

13. The patient warming system of claim 12, wherein the predetermined percentage is up to 75% higher than the percentage of power (relative to its maximum power) applied to the heating element(s) of the zone having the highest overall temperature.

14. A patient warming system, comprising
a control unit comprising:
an I/O interface comprising two or more connectors, the two or more connectors having a same configuration;
a controller configured to execute a program stored in a memory of the control unit that identifies a warming device plugged into one of the connectors and that controls application of power to the warming device relative to a set temperature and in accordance with the identity of the warming device;
warming devices interchangeably coupled to the control unit via the I/O interface, each warming device comprising:
one or more heating elements;
one or more temperature sensors; and
a connector that is configured to be coupled to any one of the two or more connectors,
wherein the one or more temperature sensors of one of the warming devices are spaced apart from an outer layer of the warming device by one or more intervening layers, and the program as executed by the controller compensate for temperature readings of the temperature sensors by applying an offset to a measured temperature, wherein the offset compensates for the difference between the measured temperature and the actual temperature at the outer layer of the warming device.

15. The patient warming system of claim 14, wherein the spacing between the temperature sensors and the outer layer of the warming device ranges from 4 millimeters to 20 millimeters.

16. The patient warming system of claim 14, wherein the offset is a constant value.

17. The patient warming system of claim 14, wherein the offset is varied depending on one or more environmental or thermal load changes.

* * * * *